(12) United States Patent
Au et al.

(10) Patent No.: US 8,236,298 B2
(45) Date of Patent: Aug. 7, 2012

(54) METHODS AND COMPOSITIONS FOR TREATMENT OF HEMATOLOGIC CANCERS

(75) Inventors: Gough Geoffrey Au, Maryland (AU); Darren Raymond Shafren, The Hill (AU)

(73) Assignee: Viralytics Limited, North Ryde, New South Wales (AU)

(*) Notice: Subject to any disclaimer, the term of this patent is extended or adjusted under 35 U.S.C. 154(b) by 1033 days.

(21) Appl. No.: 11/660,458

(22) PCT Filed: Aug. 22, 2005

(86) PCT No.: PCT/AU2005/001257
§ 371 (c)(1), (2), (4) Date: Nov. 1, 2007

(87) PCT Pub. No.: WO2006/017914
PCT Pub. Date: Feb. 23, 2006

(65) Prior Publication Data
US 2008/0193479 A1 Aug. 14, 2008

(30) Foreign Application Priority Data

Aug. 20, 2004 (AU) .............................. 2004904766
Apr. 14, 2005 (AU) .............................. 2005901879

(51) Int. Cl.
*A61K 35/76* (2006.01)
*A61K 39/125* (2006.01)

(52) U.S. Cl. .............. 424/93.6; 424/93.2; 424/93.7; 424/216.1

(58) Field of Classification Search .................. None
See application file for complete search history.

(56) References Cited

U.S. PATENT DOCUMENTS

| 7,361,354 B1 * | 4/2008 | Shafren ............ 424/199.1 |
| 2002/0037543 A1 | 3/2002 | Atkins |
| 2003/0077819 A1 | 4/2003 | Groene |
| 2008/0057036 A1 * | 3/2008 | Johansson et al. ......... 424/93.6 |

FOREIGN PATENT DOCUMENTS

| AU | 2004202292 A1 | 6/2004 |
| NZ | 534307 | 7/2004 |
| WO | WO 01/19380 * | 3/2001 |
| WO | WO 01/19380 A2 | 3/2001 |
| WO | WO 01/37866 * | 5/2001 |
| WO | WO 01/37866 A1 | 5/2001 |
| WO | WO 2004/054613 A1 | 7/2004 |
| WO | WO 2005/087931 | 9/2005 |

OTHER PUBLICATIONS

Coxsackievirus Material Safety Data Sheet of the Public Health Agency of Canada, 2001.*
Huang et al (Hybridoma 12:661-675, 1993).*
Zabala et al (Letters in Applied Microbiology 32:287-292, 2001).*
Feinman et al (Clinical Advances in Hematology & Oncology 2:162-6, 2004)03.*
Meyer et al (Virus Research 104:17-26, 2004).*
Johansson et al (Journal of Virology 78:12603-12612, 2004).*
Dufresne et al (et al (Journal of Virology 76:8966-8972, 2004).*
Girard et al (Biologicals 23:165-169, 1995).*
Emerson et al (Journal of Virology 76:8551-8559, 2002).*
Cheney et al (Journal of Virology 77:7434-7443, 2003).*
Shafren et al. "Systemic Therapy of Malignant Human Melanoma Tumors by a Common Cold-Producing Enterovirus, Coxsackievirus A21", *Clinical Cancer Research*, 10:53-60 (2004).
Hideshima et al., "NF-κB as a Therapeutic Target in Multiple Myeloma," The Journal of Biological Chemistry, vol. 277(19):16639-16647 (2002).
Kugisaki et al., "Cellular Receptors for Oncolytic Cloven-Hoofed Animal Enteroviruses," Journal of Kurume Medical Society, vol. 48(7):510-526 (1985) (English Abstract Provided).
Okada et al., "Poliovirus Infection of Established Human Blood Cell Lines: Relationship between the Differentiation Stage and Susceptibility or Cell Killing," Virology, vol. 156(2):238-245 (1987).
Tatsumi et al., "Expression of Adhesion Molecules on Myeloma Cells," Japanese Journal of Cancer Research, vol. 87(8):837-842 (1996).
Taylor et al., "Viruses as an Aid to Cancer Therapy: Regression of Solid and Ascites Tumors in Rodents After Treatment with Bovine Enterovirus," Proc. Natl. Acad. Sci. USA, vol. 68(4):836-884 (1971).

* cited by examiner

*Primary Examiner* — Mary E Mosher
(74) *Attorney, Agent, or Firm* — DLA Piper LLP (US)

(57) ABSTRACT

The present invention relates to oncolytic Picornaviruses and methods and compositions for treating subjects having hematologic cancers. These include methods and compositions for treatment of myeloma, using disclosed Picornavirus such as Coxsackievirus, in methods of direct or indirect administration to subjects and ex vivo purging of malignant cells within auto grafts prior to transplantation.

9 Claims, 19 Drawing Sheets

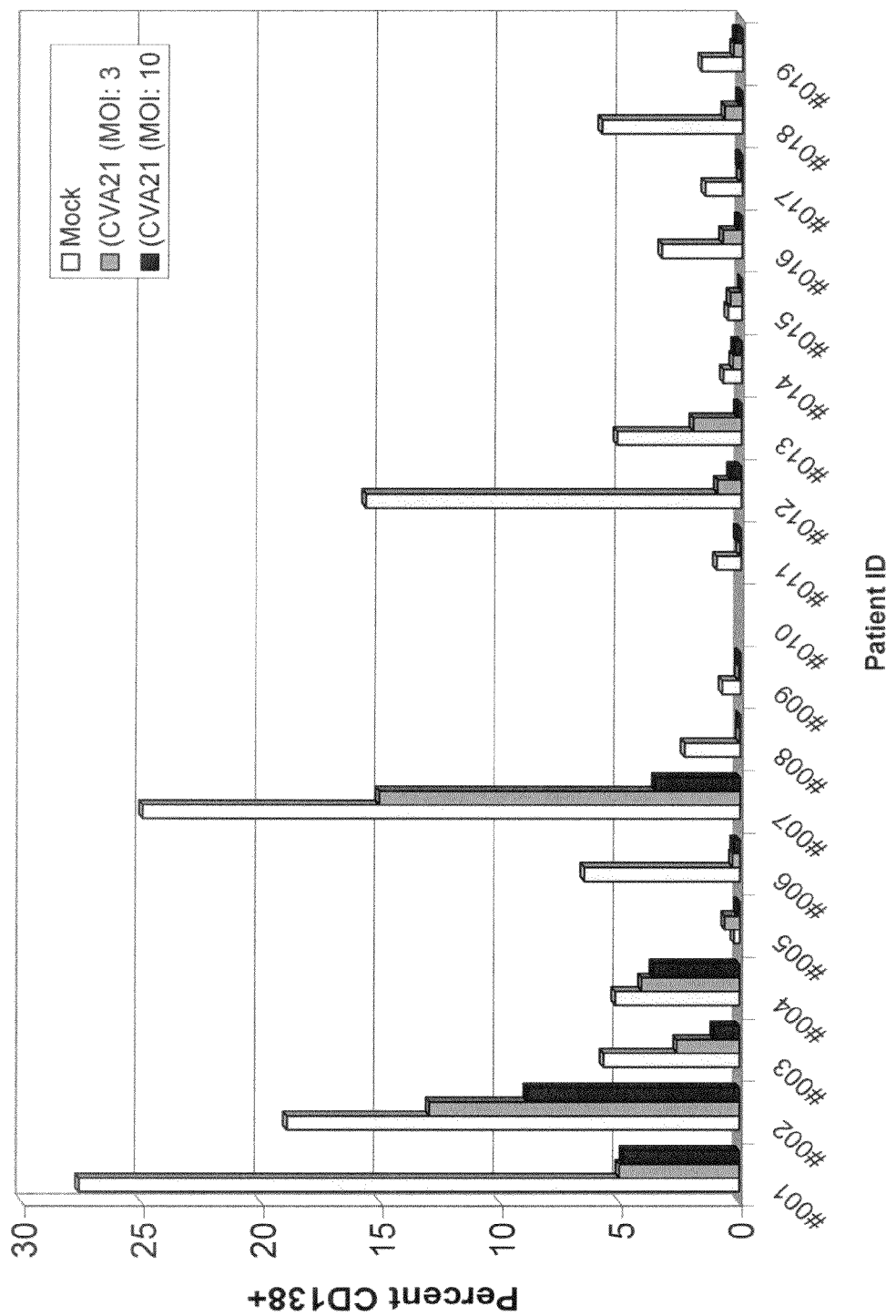
Figure 10 B(ii)

Control        Dual stain

SCOTT

JVM13

NB4

METHODS AND COMPOSITIONS FOR TREATMENT OF HEMATOLOGIC CANCERS

CROSS REFERENCE TO RELATED APPLICATIONS

This application is a 35 USC §371 National Stage application of PCT Application No. PCT/AU2005/001257 filed Aug. 22, 2005, which claims the benefit under 35 USC §119(a) to Australia Patent Application No. 2005901879 filed Apr. 14, 2005 and Australia Patent Application No. 2004904766 filed Aug. 20, 2004. The disclosure of each of the prior applications is considered part of and is incorporated by reference in the disclosure of this application.

TECHNICAL FIELD

The present invention relates to oncolytic Picornaviruses and methods and compositions for treating subjects having hematologic cancers.

BACKGROUND ART

Hematologic cancers are cancers "of the blood system." These cancers usually affect the white blood cells (disease and infection-fighting cells) rather than the red blood cells (oxygen-carrying cells). Some of these cancers are in the marrow where all blood cells are made. Some are in the lymph nodes and other lymph tissues that the white blood cells flow through. Common cancers of the white blood cells are the leukemias, Hodgkin's lymphoma, other lymphomas and multiple myeloma.

Multiple myeloma (MM) is a B-cell malignancy that accounts for approximately 1% of all types of human cancer, being more common than myelocytic leukemia or Hodgkin's disease.

Multiple myeloma can cause anemia, severe bone pain, and in some cases pathological fracture, increased risk of infection, hypercalcaemia and renal failure. While chemotherapy is the preferred initial treatment for symptomatic MM, the disease is highly resistant to chemotherapeutic agents and most patients who initially respond to such treatment eventually relapse.

A new approach in controlling cancer progression is through the use of oncolytic viruses. Oncolytic viruses are viruses that are able to selectively destroy or "lyse" malignant cells, while leaving normal host cells intact. A number of human solid cancers are susceptible to the oncolytic activity of numerous viruses, which each possess unique biologies to mediate selective oncolysis. Reovirus (Alain T, et al. *Blood.* 2002; 100:4146-4153; Thirukkumaran C M, et al. *Blood.* 2003; 102:377-387), measles virus (Grote D, et al. *Blood.* 2001; 97:3746-3754), and Newcastle disease virus (Schirrmacher V, et al. *Int J Oncol.* 2001; 18:945-952), are among three known oncolytic viruses that may be effective against some malignancies.

Recently it was demonstrated that a common cold virus, Coxsackievirus A21 (CVA21) was effective against human melanoma xenografts in an immune-deficient mouse model (Shafren D R, et al. *Clin Cancer Res.* 2004; 10:53-60). CVA21 is an enterovirus known to selectively utilize the cell surface molecules intercellular-adhesion molecule 1 (ICAM-1) and decay-accelerating factor (DAF) to mediate infection of cells. Although CVA21 can bind to DAF, ICAM-1 is the key receptor for CVA21 infection of cells—as without ICAM-1 expression on the cell surface, CVA21 is unable to gain cell entry and attain infection of the host cell under normal conditions.

The present applicant previously developed new methods for treating solid tumor malignancies using oncolytic viruses that recognise ICAM-1 (PCT/AU00/01461 (WO 01/37866) entitled "A Method of Treating a Malignancy in a Subject and a Pharmaceutical Composition For Use in Same"). Excellent therapeutic results were obtained by using various Coxsackievirus A strains on a number of solid tumor cell types. New methods for the treatment of abnormal cells, such as cancer cells, in mammals using viruses such as Echoviruses which recognise integrin $\alpha_2\beta_1$ for infectivity of the cells were also developed by the present applicant (PCT/AU2003/001688 (WO2004/054613) entitled "A method of treating a malignancy in a subject via direct Picornaviral-mediated oncolysis"). In order to expand the possible cancer treatment and provide even more efficacious treatments, the present inventors have surprisingly found that Picornavirus isolates may also be suitable as oncolytic agents in hematologic cancers.

SUMMARY OF INVENTION

In a first aspect the present invention provides a method for treating and/or preventing hematologic cancer in a subject, the method comprising administering a therapeutically effective amount of a Picornavirus or a modified form thereof such that at least some cells of the cancer undergo viral oncolysis.

In a second aspect the present invention provides a method for treating and/or preventing hematologic cancer in a subject, the cancer selected from the group consisting of multiple myeloma, B cell lymphoma, B prolymphocytic leukemia and monocytic leukemia, the method comprising administering a therapeutically effective amount of a Picornavirus or a modified form thereof such that at least some cells of the cancer undergo viral oncolysis.

In a preferred form of the invention the subject is a human. The Picornavirus may be any Picornavirus including known and classified Picornavirus and yet to be classified Picornavirus. Preferably, the Picornavirus is selected from the group consisting of both prototype and clinically isolated strains. In one preferred method the Picornavirus is an enteroviruses including Coxsackievirus, Echovirus, Poliovirus and unclassified enteroviruses, or from other genera of picornaviruses which may include Rhinovirus, Paraechovirus, Hepatovirus, Cardiovirus, Aphthovirus, Erbovirus, Kobovirus and Teschovirus.

In a preferred form, the Picornavirus is a Coxsackievirus. Preferably, the Coxsackie A group virus is selected from the group consisting of CVA13, CVA15, CVA18, CVA20, CVA21, modified forms thereof, and combinations thereof. More preferably, the Coxsackie A group virus is selected from CVA13, CVA15, CVA18, CVA20 or CVA21.

In a preferred form, the Coxsackie A group virus is CVA15 or CVA21. Preferably, the Coxsackie A group virus is CVA15. More preferably the CVA15 is G-9.

In another preferred form, the Coxsackie A group virus is CVA21. More preferably, the CVA21 is Kuykendall strain.

As used herein, the term 'hematologic cancer' includes non-solid tumors such as leukemia, multiple myeloma, Hodgkin's disease, non-Hodgkin's disease, Myelodysplasia, and lymphoma, such as B cell lymphoma. Examples of leukemia include, but are not limited to chronic myelogenous leukemia, acute lymphocytic leukemia (ALL), chronic and lymphocytic leukemia (CLL), B prolymphocytic leukemia and monocytic leukemia. In a preferred form, the hematologic cancer is multiple myeloma.

In a preferred form, the hematologic cancer is, or comprises cells which are, resistant to one or more chemotherapeutic agent(s).

In a preferred form, the Picornavirus is administered to a human subject in any suitable manner. For example the virus may be administered intravenously, intratumorally, intraperitoneally, intramuscularly, intraocularly, subcutaneously, orally, topically or by ex vivo purging of malignant cells within auto grafts prior to autologous stem cell transplantation. In one form, the method comprises prophylactic treatment, for example for MGUS. In one form, the method comprises a systemic anti-tumor agent for hematologic cancer, for example multiple myeloma. In one form the method comprises the ex vivo purging of malignant cells within auto grafts prior to transplantation. Preferably the auto grafts comprise hematopoietic stem cells.

In a preferred form, the range of viral dose may be between about 0.01 to about 1000 infectious viral units per cell.

In one preferred form, the virus may be administered to a subject in combination with an effective amount of a chemotherapeutic agent.

In another preferred form, the virus may be administered to a subject in combination with an effective amount of a probiotic agent.

The cells of the hematologic cancer may over-express the virus-cell entry receptor molecules intercellular adhesion molecule-1 (ICAM-1) and/or decay-accelerating factor (DAF).

The cells of the hematologic cancer may constitutively express $NF-_\kappa B$.

In a third aspect, the present invention provides a method for treating and/or preventing hematologic cancer in a subject, the method comprising administering a therapeutically effective amount of a nucleic acid molecule derived from a Picornavirus or a modified form thereof such that at least some cells of the cancer are killed by the virus.

The nucleic acid molecule may be single stranded RNA or complementary DNA from the virus.

In a preferred form, the Picornavirus is a Coxsackievirus. Preferably, the Coxsackievirus is type A, more preferably Coxsackievirus A21 (CVA21). Preferably the CVA21 is Kuykendall strain.

In a fourth aspect, the present invention provides a pharmaceutical composition for use in treating and/or preventing hematologic cancer in a subject, the composition comprising an effective amount of a Picornavirus or a modified form thereof, capable of lytically infecting a hematologic cancer, together with a pharmaceutically acceptable excipient, diluent or carrier.

Pharmaceutically acceptable excipients, diluents or carriers will be well known by those skilled in the art and include, but are not limited to, any inert substance capable of being used as a vehicle for administration of a therapeutic agent. In a preferred form, the pharmaceutically acceptable carrier may be a liposome.

In a fifth aspect, the present invention provides a pharmaceutical composition for use in treating and/or preventing hematologic cancer in a subject, the composition comprising an effective amount of a nucleic acid molecule derived from a Picornavirus or a modified form thereof, capable of lytically infecting a hematologic cancer, together with a pharmaceutically acceptable excipient, diluent or carrier.

In a preferred form, the pharmaceutical composition further comprises liposomes that may also contain monoclonal antibodies that bind to specific tumour markers, allowing targeting of the nucleic acid-liposome complex:

In a sixth aspect, the present invention provides a method of treating and/or preventing hematologic cancer in a subject, comprising administering a therapeutically effective amount of a pharmaceutical composition according to the third or fourth aspects of the present invention such that at least some cells of the cancer undergo viral oncolysis.

In a seventh aspect, the present invention provides use of a Picornavirus or a modified form thereof, capable of lytically infecting a hematologic cancer, together with a pharmaceutically acceptable excipient or diluent in a method of treating and/or preventing hematologic cancer in a subject.

In an eighth aspect, the present invention provides use of a nucleic acid molecule derived from a Picornavirus or a modified form thereof, capable of lytically infecting a hematologic cancer, together with a pharmaceutically acceptable excipient or diluent in a method of treating and/or preventing hematologic cancer in a subject.

In a ninth aspect, the present invention provides use of a Picornavirus or a modified form thereof, capable of lytically infecting a hematologic cancer, in the manufacture of a medicament for treating and/or preventing hematologic cancer in a subject.

In a tenth aspect, the present invention provides use of a nucleic acid molecule derived from a Picornavirus or a modified form thereof, capable of lytically infecting a hematologic cancer, in the manufacture of a medicament for treating and/or preventing hematologic cancer in a subject.

In an eleventh aspect, the present invention provides a method for inducing an immune response in a mammal against hematologic tumor or cancer cells, the method comprising infecting said cells in the mammal with a therapeutically effective amount of a Picornavirus or a modified form thereof such that at least some cells of the cancer undergo viral oncolysis.

Throughout this specification, unless then context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field, in Australia or elsewhere, relevant to the present invention before the priority date of this application.

In order that the present invention may be more clearly understood, preferred forms will be described with reference to the following drawings and examples.

ABBREVIATIONS

The abbreviation "MM" is used herein for multiple myeloma.

The abbreviation "CVA" is used herein for Coxsackie A group virus, for example CVA21 is an abbreviation for Coxsackievirus A21. The literature in this field variously uses the abbreviations "CAV" and "CVA" Coxsackie. A group virus and it will be understood for the purposes of the present application that the abbreviations refer to the same organisms and so are interchangeable.

The abbreviation "MOI" is used herein for multiplicity of infection.

The abbreviation "MGUS" is used herein for monoclonal gammopathy of undetermined significance.

The abbreviation "BM" is used herein for bone marrow.

The abbreviation "CFU-GM" is used herein for colony forming units granulocyte/macrophage.

The abbreviation "MTT assay" is used herein for microculture tetrazolium assay which uses the chemical 3-(4,5-dimethylthiazol-2-yl)-2,5-diphenyltetrazoliumbromide.

The abbreviation "PI" is used herein for propidium iodide.

The abbreviation "PBMC" is used herein for peripheral blood mononuclear cells.

The abbreviation "BMSC" is used herein for bone marrow stromal cells.

The abbreviation "mAb" is used herein for monoclonal antibody.

The abbreviation "$TCID_{50}$" is used herein for tissue culture infectious dose 50%.

The abbreviation "PFU" is used herein for plaque forming units.

The abbreviation "CPE" is used herein for cytopathic effect.

The abbreviation "ICAM-1" is used herein for intercellular-adhesion molecule 1.

The abbreviation "DAF" is used herein for decay-accelerating factor.

The abbreviation "kb" is used herein for kilobase.

The abbreviation "DNA" is used herein for deoxyribonucleic acid.

The abbreviation "RNA" is used herein for ribonucleic acid.

The abbreviation "ELISA" is used herein for enzyme-linked immunosorbent assay.

Multiple myeloma cell lines RPMI-8226, U266 and NCI-H929 cells and normal PBMCs were dual stained with anti-ICAM-1 and anti-DAF mAbs. The anti-ICAM-1 mAb was directly conjugated with FITC and the anti-DAF mAb was stained indirectly via a secondary conjugate linked to PE.

Figure 2:
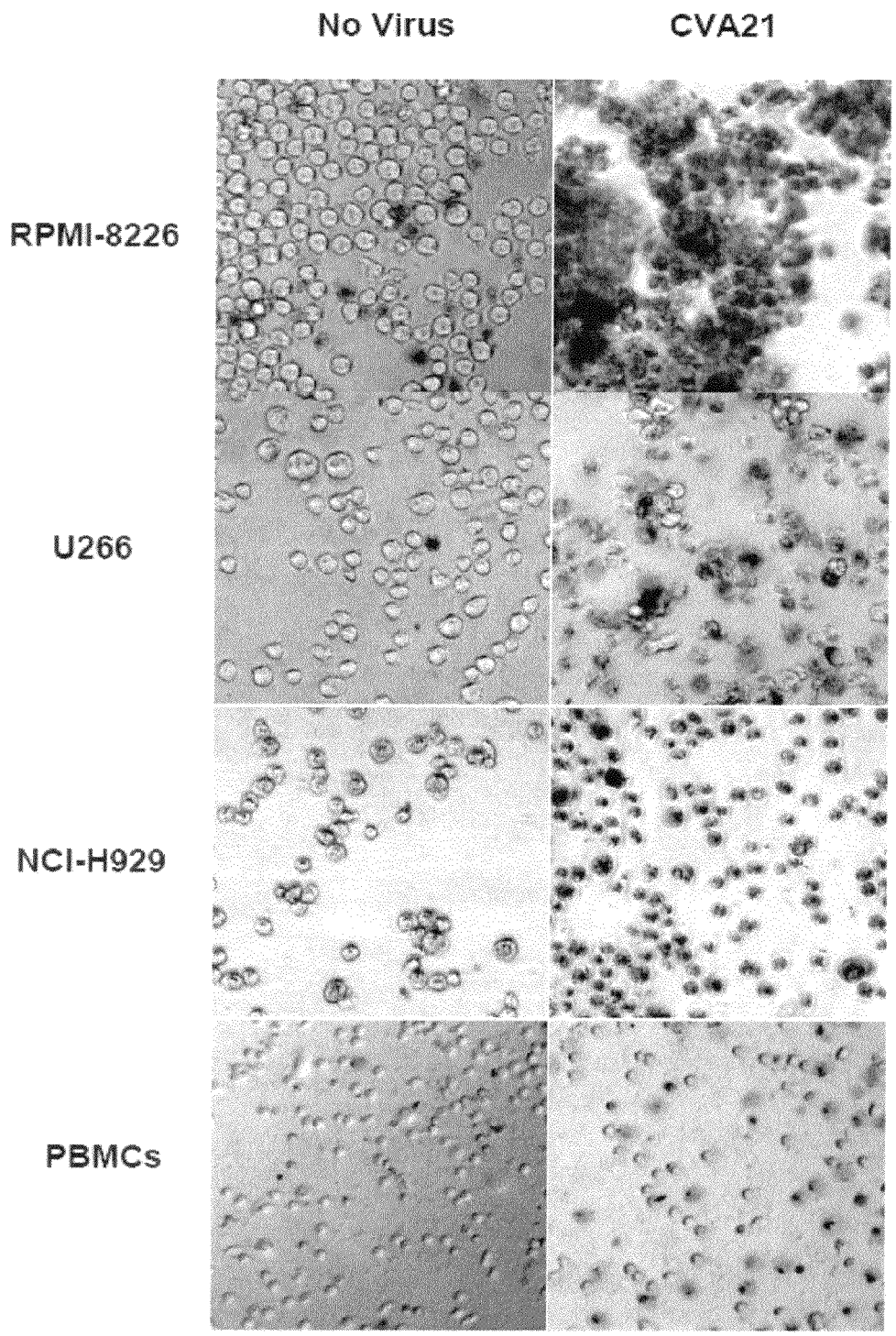

FIG. 2. Cytopathic effect of CVA21 on multiple myeloma cell lines. To assess the cytopathic effect of CVA21 on multiple myeloma cell lines and normal PBMCs, cultures of RPMI-8226, U266, NCI-H929 and PBMCs in 6-well plates were incubated with or without CVA21 for 48 h at 37° C. (MOI~1). The cell supernatant was carefully aspirated of each of the wells, and the cells were stained with a 0.01% trypan blue solution. Non-viable cells destroyed by CVA21 infection were stained positively with the trypan blue, while the viable cells were able to exclude the dye. Photomicrographs were taken at ×100 magnification.

Figure 3:
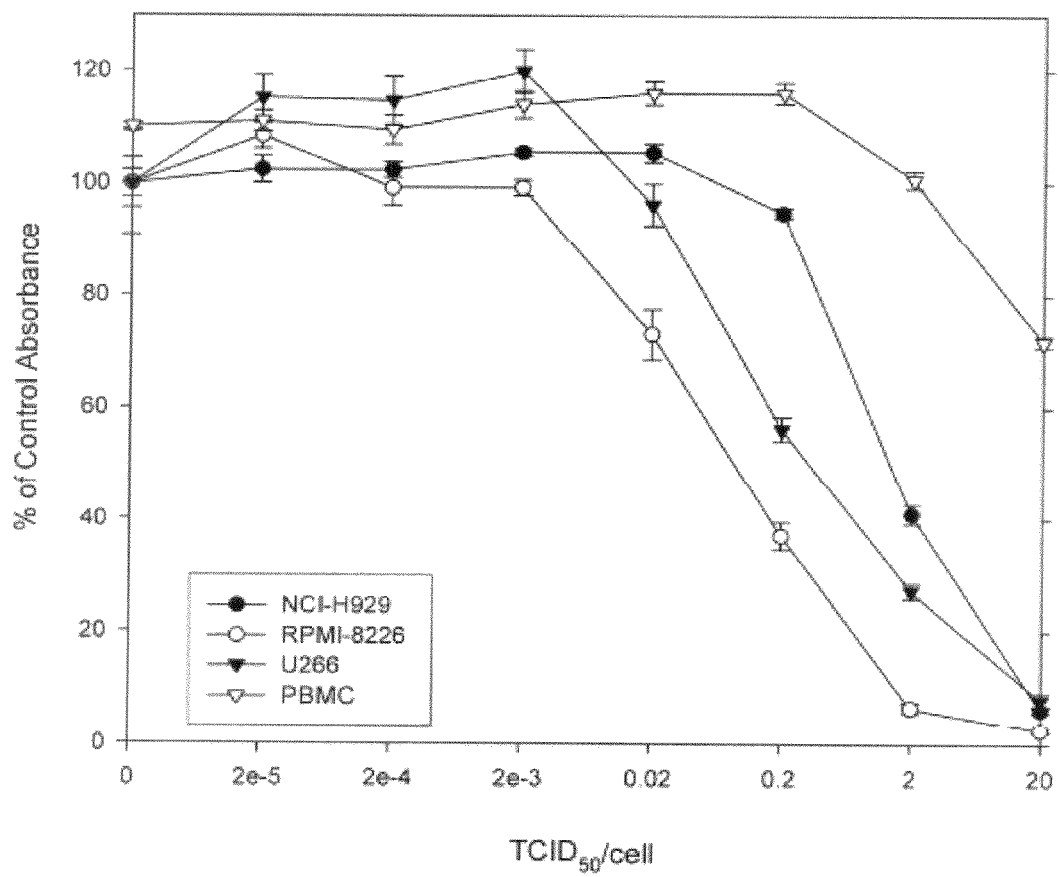

FIG. 3. Oncolytic action of CVA21 on MM cell lines and normal PBMCs using the MMT assay.

MM cell lines RPMI-8226, U266 and NCI-H929 and normal PBMCs demonstrating differential sensitivity to continuous CVA21 for 48 h. Error bars indicate is the standard error mean of quadruplicate wells/group.

Figure 4:
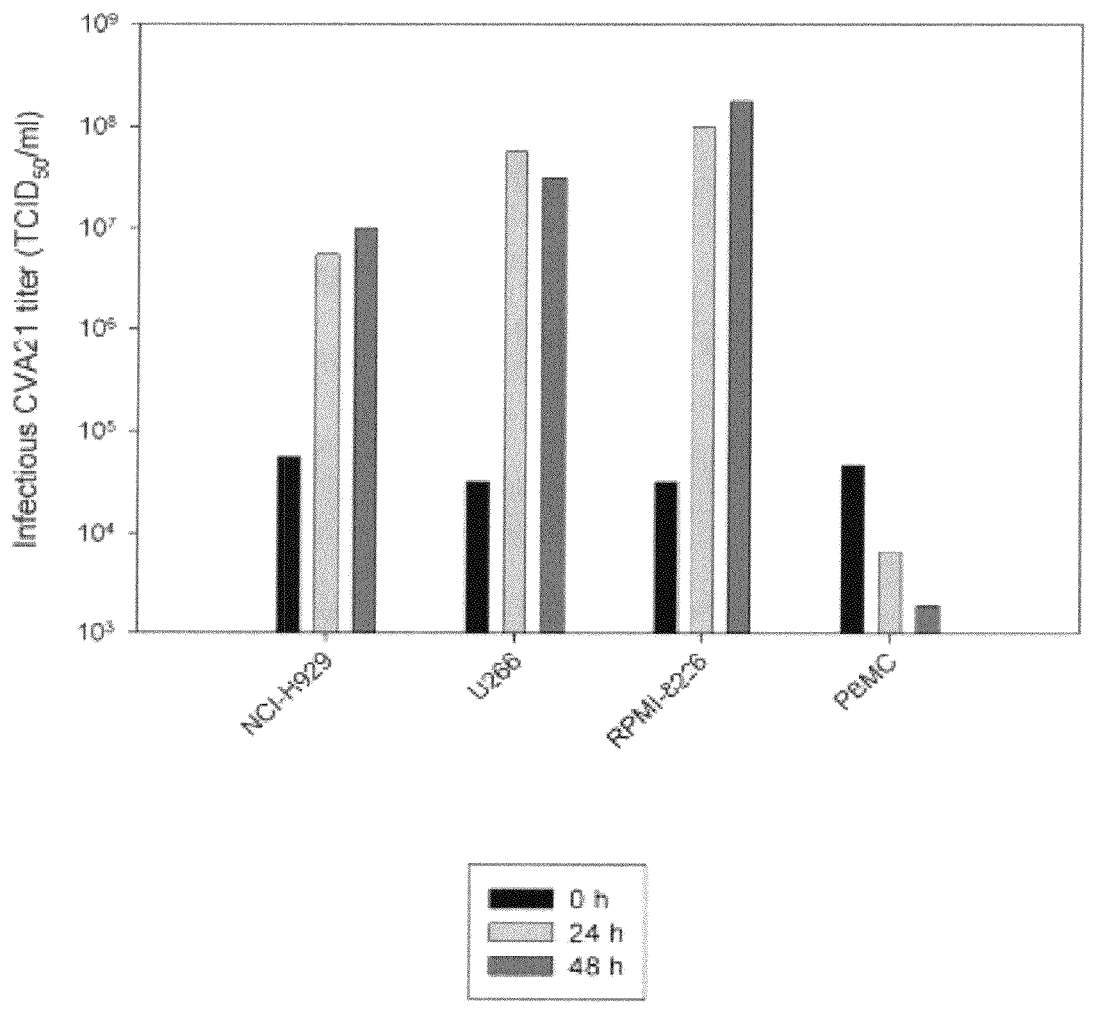

FIG. 4. CVA21 yield post infection of multiple myeloma cell lines.

Capacity of MM cell lines NCI-H929, U266 and RPMI-8226 to yield infectious virus particles post infection with CVA21 for 24 h and 48 h. Following infection with ~1 MOI of CVA21, increases of virus can be detected in each of the multiple myeloma cells lines, as opposed to the normal PBMCs.

Figure 5:
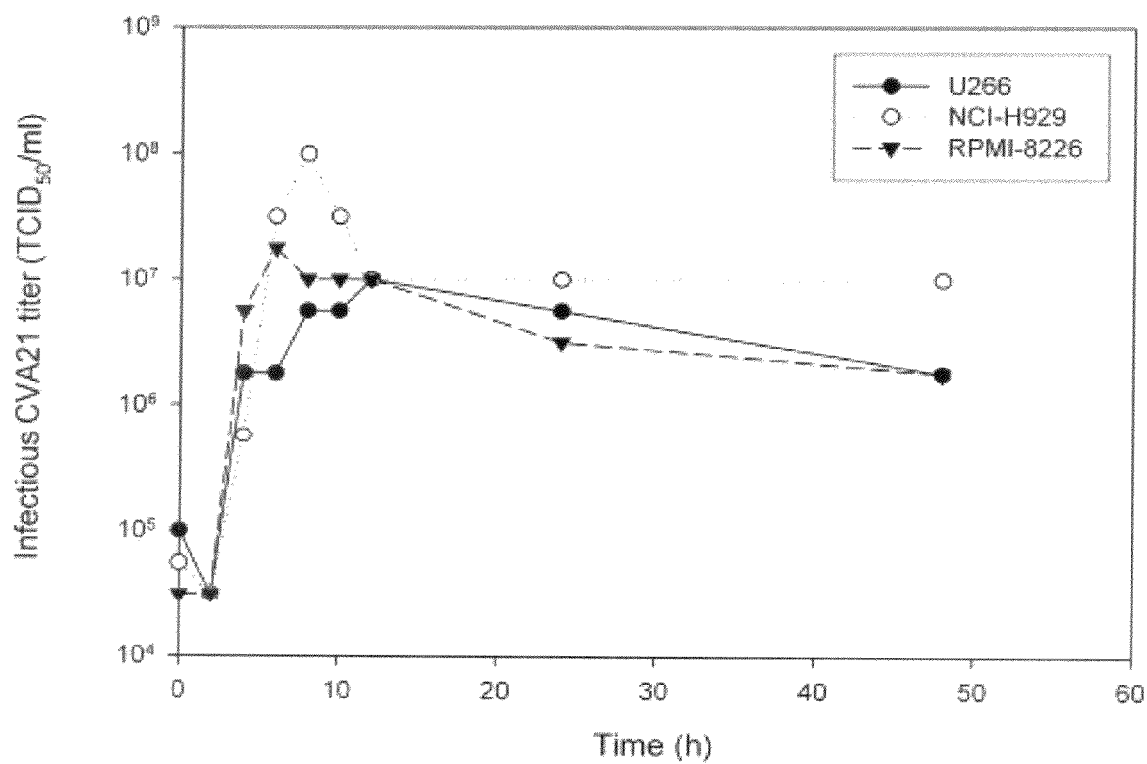

FIG. 5. Viral growth curve of CVA21 in multiple myeloma cells. Viral growth curve of CVA21 in U266 (●), NCI-H929 (○) and RPMI-8226 (▼) cell lines following synchronous infection (multiplicity of infection approx. 1) and collection of viral offspring at the indicated time intervals. The titration of samples was performed in triplicate and the average virus yield at each time point was plotted.

Figure 6:
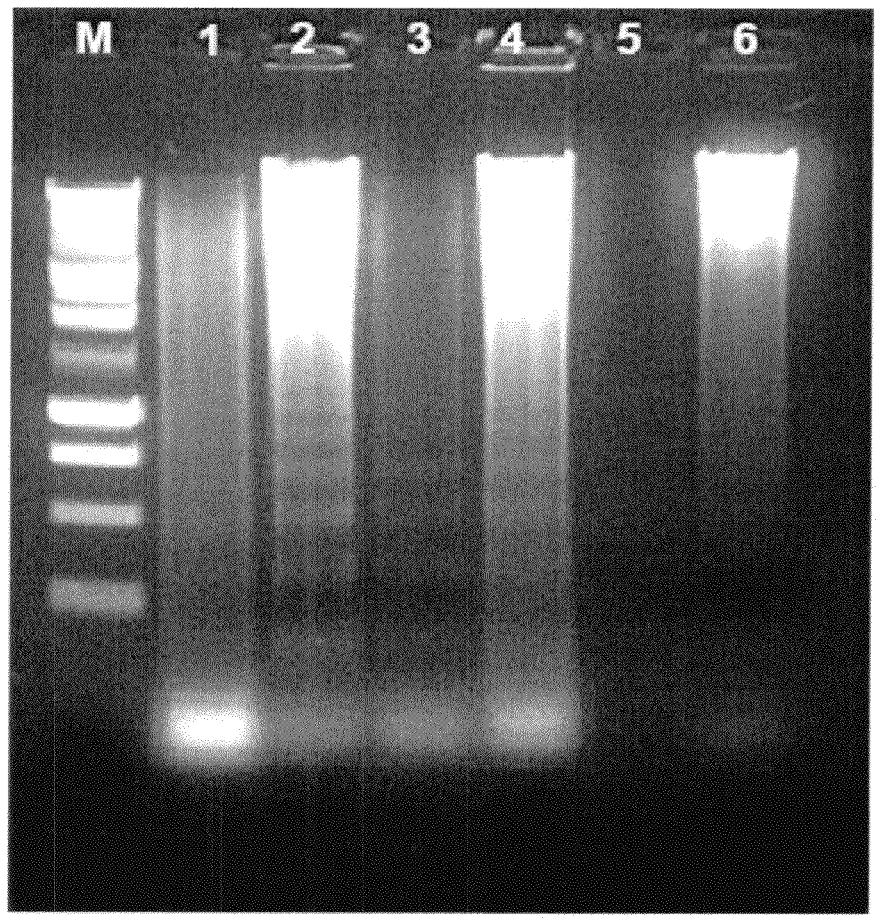

FIG. 6. Analysis of DNA fragmentation in RPMI-8226, NCI-H929, and U266 cells infected with CVA21.

RPMI-8226, NCI-H929 and U266 cells were infected for 24 h with CVA21 (MOI~10 $TCID_{50}$/cell). Total DNA was extracted from infected and non-infected cells, and fragmentation was assessed by agarose gel electrophoresis. DNA samples from myeloma cell lines RPMI-8226 (lanes 1 and 2), NCI-H929 (lanes 3 and 4) and U266 (lanes 5 and 6) are shown. Lane "M" contains the 1-kb DNA ladder. The DNA extracted from MM cell lines cultured in medium alone are shown in lanes 1, 3 and 5, whereas lanes 2, 4 and 6 contain the cellular DNA extracted from cell lines treated with CVA21.

Figure 7:
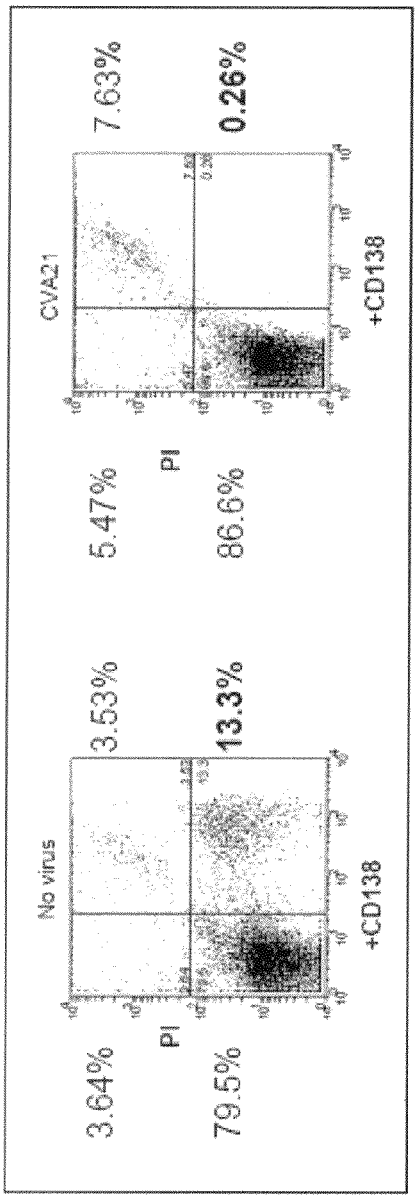
Figure 7:
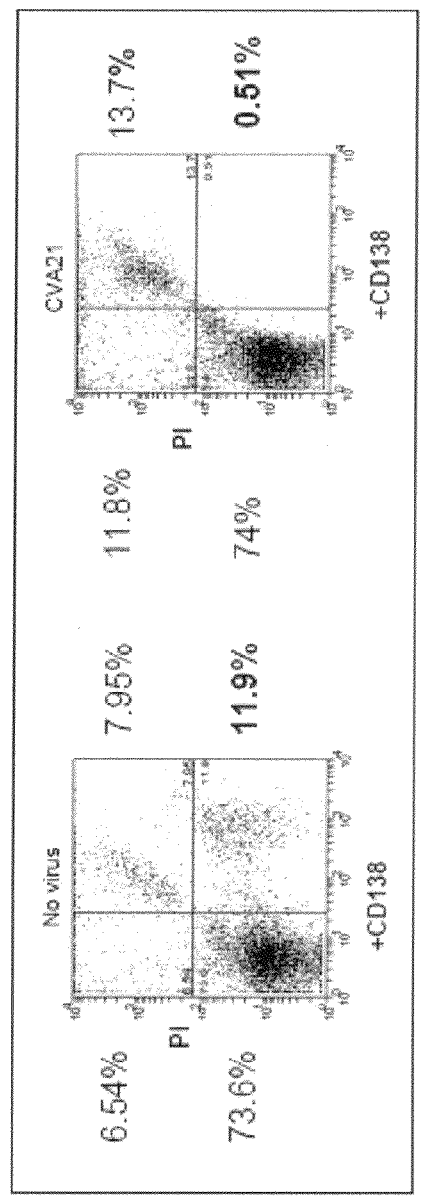

FIG. 7. Ex vivo purging of multiple myeloma cells from mixtures with PBMCs.

Mixtures of normal PBMCs and multiple myeloma cells RPMI-8226 and U266 were cultured together and infected with CVA21 for 3 days to assess the efficiency of multiple myeloma purging. Viable myeloma cells ($CD138^+/PI^-$) and PBMCs ($CD138^-/PI^-$) were analyzed by flow cytometry. Flow cytometric plots of purged ("CVA21") and unpurged ("no virus") samples are shown for both RPMI-8226 and U266 cell lines.

Figure 8A:
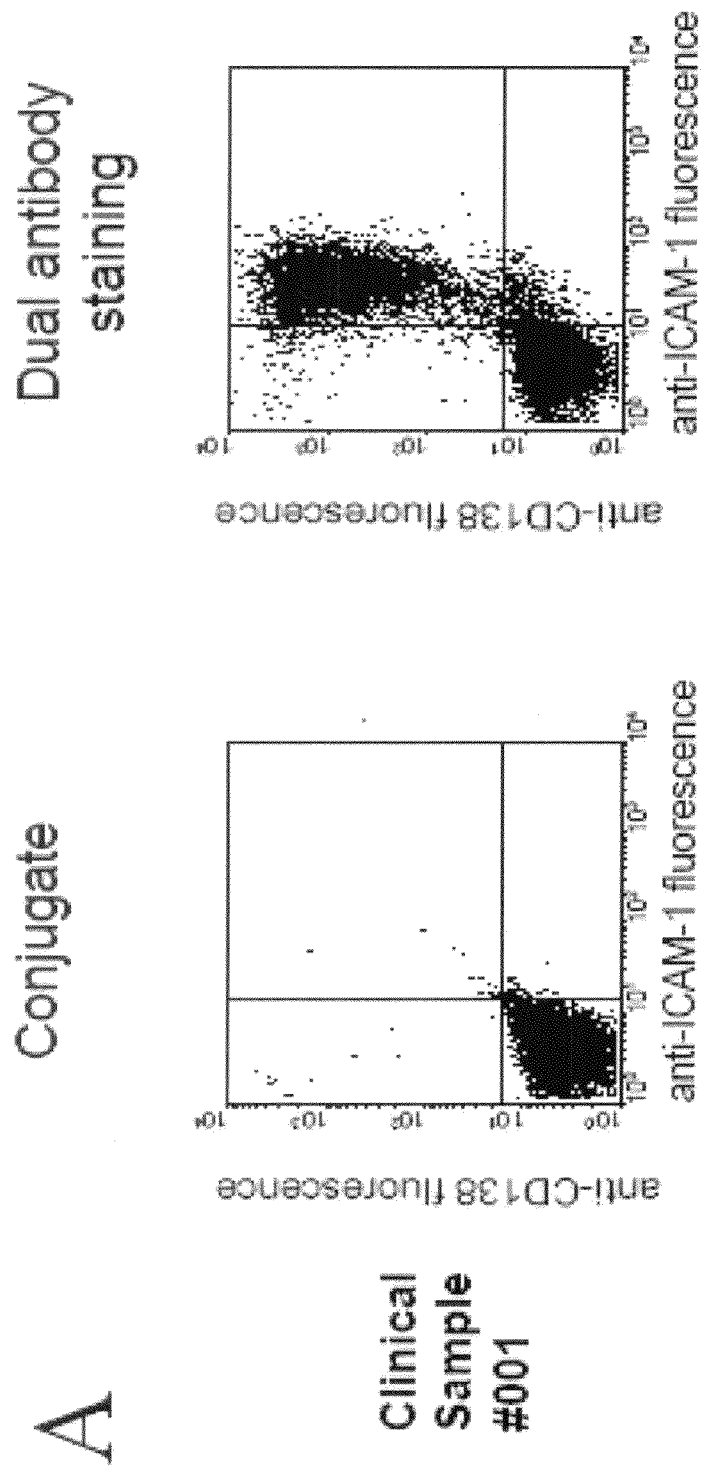

FIG. 8. Analysis of ICAM-1 expression on clinical multiple myeloma samples and growth inhibition of CVA21.

(A) A patient bone marrow aspirate was obtained from a multiple myeloma patient (clinical sample #001) and processed to obtain a single cell suspension. Cells were dual stained with anti-CD138 and anti-ICAM-1 antibodies. Myeloma cells that were positive for ICAM-1 expression appear in the upper right quadrant of the dot plot ($CD138^+/ICAM-1^+$). Approximately 37% of the cells in the primary tumor sample is consisted of $CD^{138+}$ plasma cells.

(B) The clinical bone marrow cells from the patients was then infected with CVA21 at various concentrations, and cancer cell growth inhibition was assessed by a MTT assay. The graph indicates the percentage of cell survival at the different inputs of virus for sample #001.

FIG. 9. Capacity of CVA21 to purge multiple myeloma plasma cells from clinical bone marrow samples.

(A) The bone marrow sample from patient #001, was incubated with either no virus, ~2.75 $TCID_{50}$/cell, 5.5 $TCID_{50}$/cell or ~11 $TCID_{50}$/cell and incubated for 72 h before analysing with flow cytometry to assess the percentage of myeloma cells still alive. Cells were dual stained with propidium iodide, and the anti-CD138-FITC antibody. The live myeloma cells remaining after purging with different concentrations of virus can be seen in the bottom right quadrants of each dot plot ($CD138^+/PI^-$).

(B) Photomicrographs of CVA21 infected primary tumor samples infected with 0, ~2.75 and ~5.5 $TCID_{50}$/cell for 48 h. Cell clumping can be seen in both virus treated samples compared to the no virus control (×40 magnification).

(C) The percentage of viable myeloma cells following challenge with different concentrations of virus, calculated from the flow cytometry data above.

Figure 10:
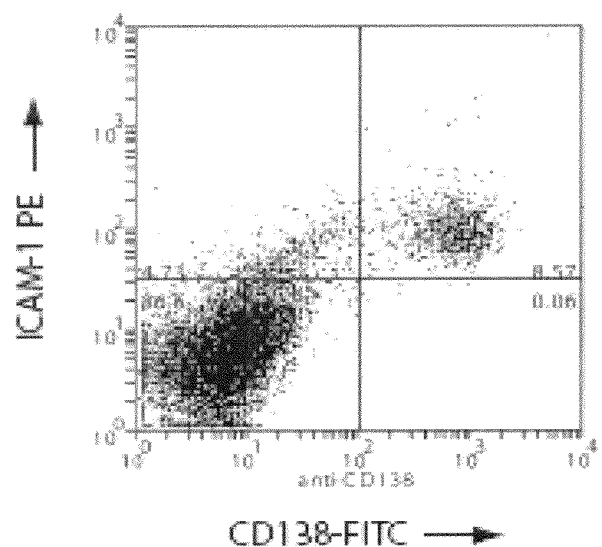
Figure 10:
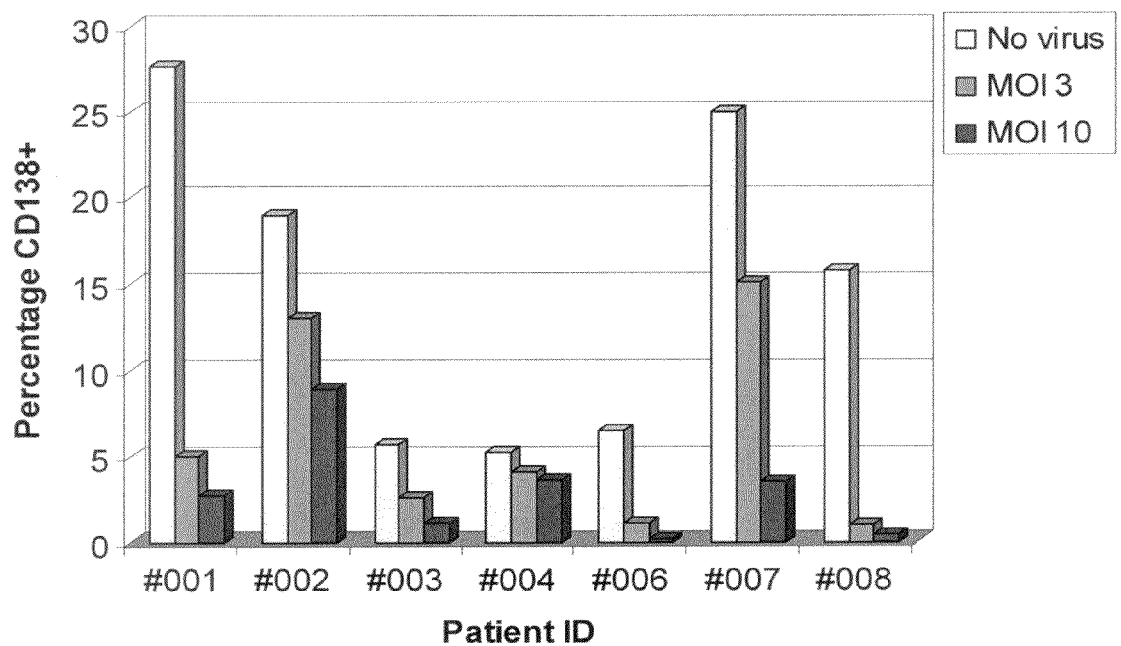
Figure 10:
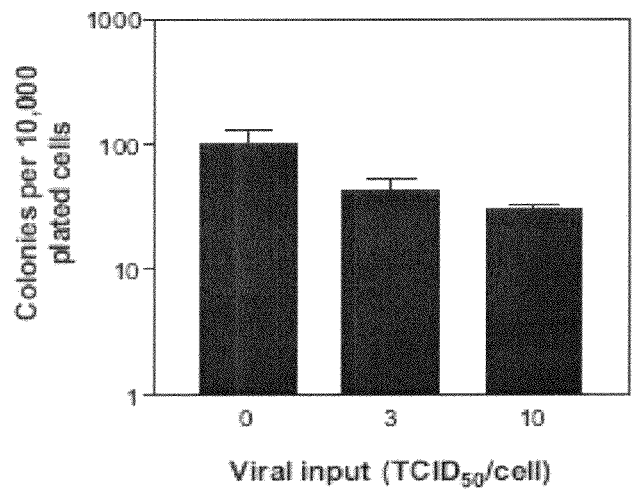
Figure 10:
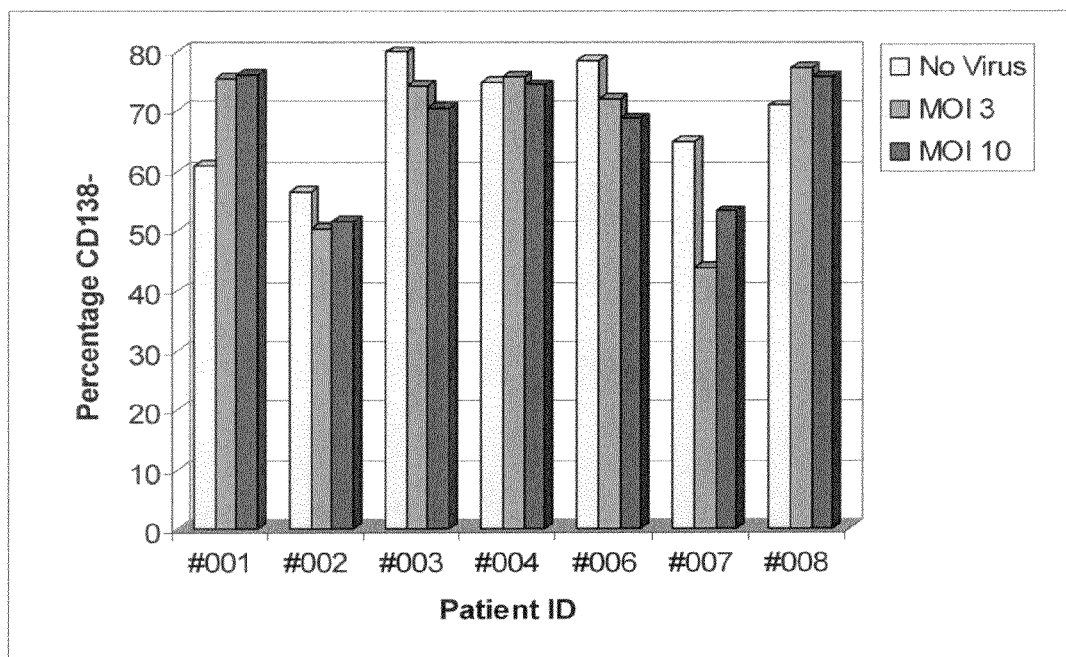

FIG. 10. CVA21 selectively purges plasma cells from MM and MGUS BM.

(A) ICAM-1 expression on $CD138^+$ cells. A representative dot plot from patient #005 following staining with anti-CD138 and anti-ICAM-1.

(B)(i) In vitro infection and killing of BM samples from patients with relapsed MM (#001, #002 and #008), MM in partial remission (#003); monoclonal gammopathy of undetermined significance (MGUS) (#004, #006) and MM at diagnosis (#007). BM samples from the seven patients were infected in vitro with CVA21 at a multiplicity of infection (MOI) of 0 (mock), 3 or 10 $TCID_{50}$ per cell. Samples were collected 48 hours post infection and analyzed by flow cytometry after staining for CD138. 10,000 events were recorded per sample; percentages of viable cells that were CD138 positive are indicated.

(B)(ii). Cumulative results for a total of 19 clinical samples with a range of conditions as indicated in Table 1 herein.

(C) BM progenitors are resistant to CVA21. Residual cells from three BM samples infected with CVA21 at MOIs of 0 (mock), 3 and 10, $TCID_{50}$ per cell for 48 hours (approximately 10,000 cells) were cultured in 3 ml of MethoCult GF4434 complete methylcellulose culture medium (Stem Cell Technologies, Vancouver, Canada). The CFU-GM cultures were performed in wells of a 6-well plate and incubated for 14 days at 37° C., 5% $CO_2$. CFU-GM were scored as colonies consisting of granulocytes and/or macrophages of 20 or more cells using an inverted microscope. The average number of colonies following infection with CVA21 at each concentration is shown. Error bars indicate the standard error of the mean of the three samples. Number of colonies shown is per $1 \times 10^4$ cells plated. CFU-GM, colony forming units granulocyte/macrophage.

(D) PBMCs ($CD138^-$) populations were still viable following CVA21 purging as assessed by flow cytometry. Following infection of the seven patient BM samples described above in (B)(i), $CD138^-$ cells were also quantitated. This population remained relatively unchanged following CVA21 infection.

(E) In vitro infection and killing of BM samples from patients as described in FIG. 10B(ii), with results expressed as percentage reduction of $CD138^+$ cells.

FIGS. 11(A and B). Flow cytometric analysis of ICAM-1 and DAF on B cell lymphoma, B prolymphocytic leukemia, acute promyelocytic leukemia (APML), monocytic leukemia and multiple myeloma cell lines.

(A) B cell lymphoma cell line SCOTT, B prolymphocytic leukemia cell line JVM13, acute promyelocytic leukemia (APML) cell lines NB4 and (B) HL-60, monocytic leukemia cell line U937 and multiple myeloma cell line H929 were dual stained with anti-ICAM-1 and anti-DAF mAbs. The anti-ICAM-1 mAb was directly conjugated with FITC and the anti-DAF mAb was stained indirectly via a secondary conjugate linked to PE.

Figure 12:
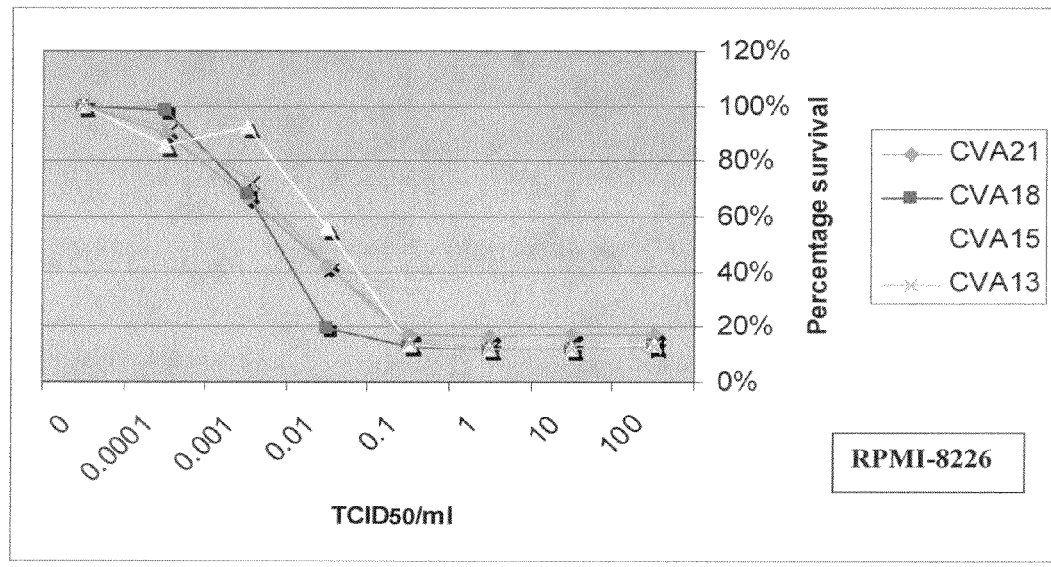
Figure 12:
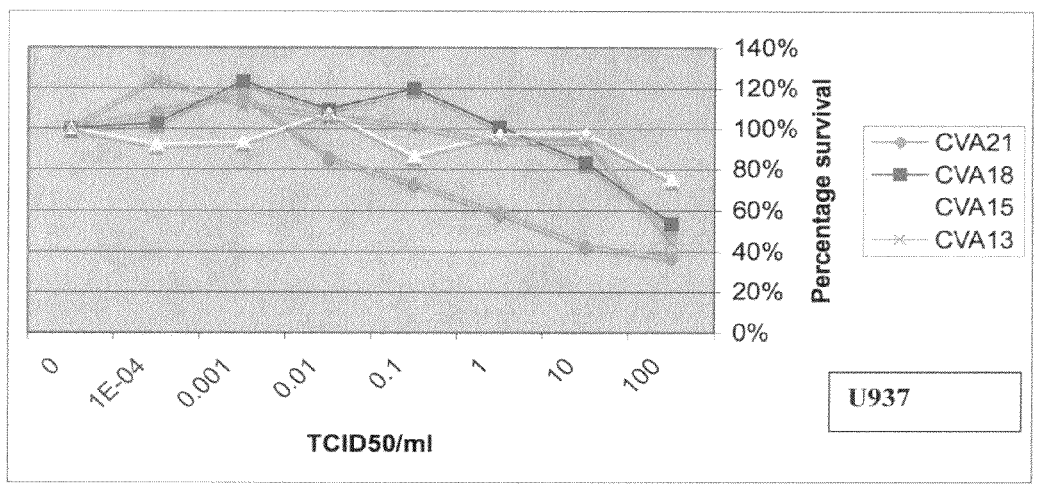
Figure 12:
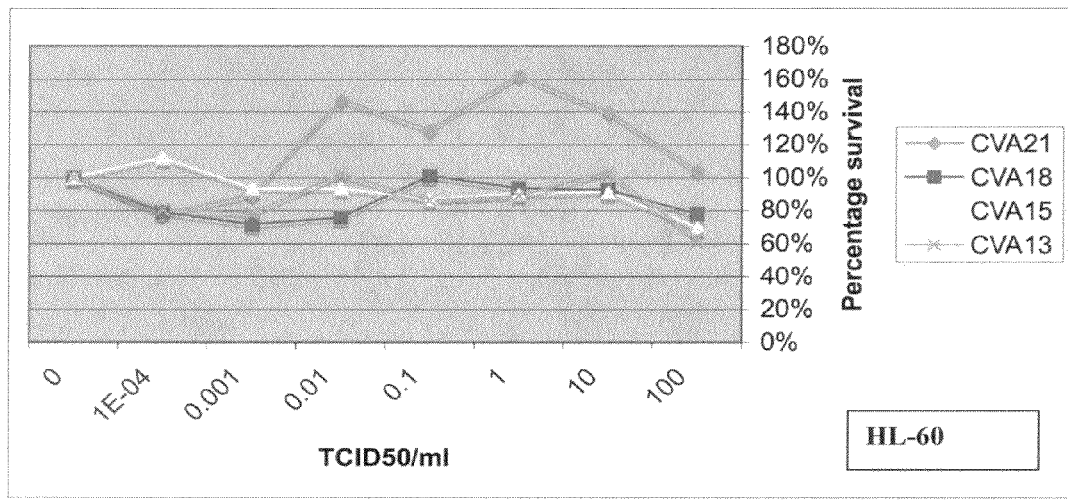

FIG. 12. Oncolytic action of CVA21, CVA18, CVA15 and CVA13 on selected hematologic cancer cell lines using MMT assay.

(A) MM cell line RPMI-8226, (B) monocytic leukemia cell line U937 and (C) acute promyelocytic leukemia (APML) cell line HL-60 demonstrating differential sensitivity to continuous virus as indicated for 48 h.

Figure 13:
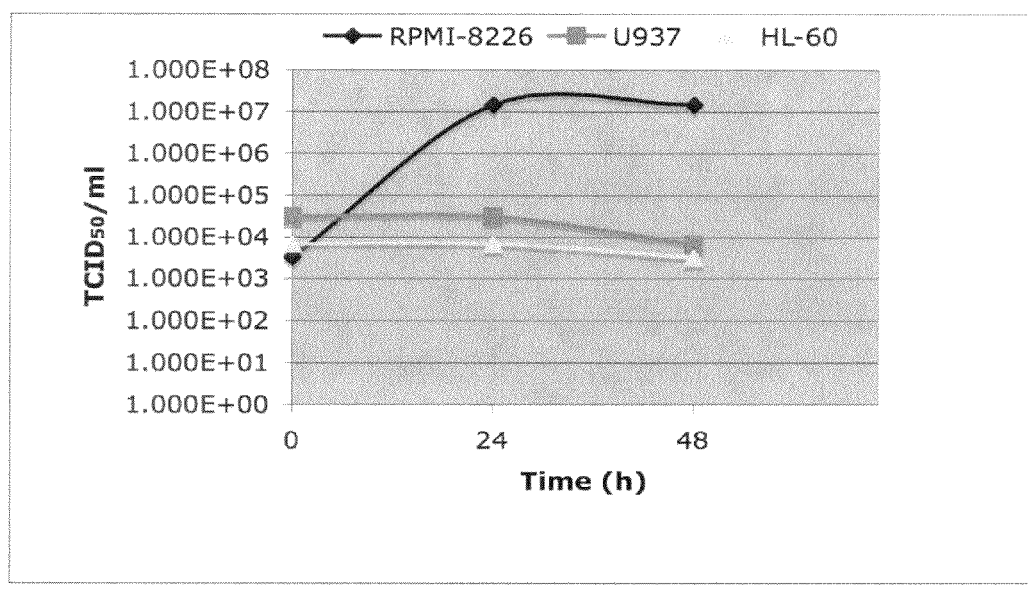

FIG. 13. CVA21 yield post infection of selected hematologic cancer cell lines.

Capacity of (◇) MM cell line RPMI-8226, (□) monocytic leukemia cell line U937 and (Δ) acute promyelocytic leukemia (APML) cell line HL-60 to yield infectious virus particles post infection with CVA21 for 24 and 48 h. Following infection with ~10 $TCID_{50}$/cell of CVA21, increases of virus were detected only in MM cell line RPMI-8226.

PREFERRED MODE(S) FOR CARRYING OUT THE INVENTION

Although it is known that some naturally occurring Picornavirus and other viruses such as reoviruses are suitable for use in treatment of limited types of cancers, there is still a need to develop improved treatments.

As described herein, the present inventors have discovered that Picornaviruses can be used to lytically infect hematologic tumors or cancers. Cells that are "susceptible" are those that demonstrate induction of cytopathic effects, viral protein synthesis, and/or virus production.

Based upon these discoveries, the present inventors have developed methods and compositions for treatment and/or prophylaxis of hematologic cancers in mammals. The mammal may be any mammal in need of treatment according to the invention. The mammal may be a human or an individual of any species of social, economic or research importance including, but not limited to, mice, dogs, cats, sheep, goats, cows, horses, pigs, non-human primates, and humans. In a preferred embodiment, the mammal is a human.

Death of the cells will typically result from infection of the cells by the virus, and may be caused by either lysis of the cells due to intracellular replication of the virus or by infection triggering apoptosis most likely as a result of the activation of cellular caspases. Once lysed, the cytosolic contents of infected cells may spill from the ruptured plasma membranes, and antigens including cell surface antigens capable of eliciting an immune response to the abnormal cells may be released. Hence, treatment of hematologic tumor or cancer cells, in a mammal in accordance with a method of the invention may provide a boost to the immunity of the mammal against such cells.

The Picornavirus may be any Picornavirus including known and classified Picornavirus and yet to be classified Picornavirus. The Picornavirus may be selected from the group consisting of both prototype and clinically isolated strains. Representative types of human Picornavirus include enteroviruses, Coxsackievirus, Echovirus, Poliovirus, and unclassified enteroviruses, Rhinovirus, Paraechovirus, Hepatovirus, and Cardiovirus. In one preferred method the Picornavirus is an enteroviruses including Coxsackievirus, Echovirus, Poliovirus and unclassified enteroviruses, or from other genera of picornaviruses which may include Rhinovirus, Paraechovirus, Hepatovirus, Cardiovirus, Aphthovirus, Erbovirus, Kobovirus and Teschovirus. In a preferred form, the Picornavirus is a Coxsackievirus. Preferably, the Coxsackievirus is type A, more preferably Coxsackievirus A21.

Desirably, the virus may be selected from Coxsackie A-group viruses. CVA21 is preferred and in particular CVA21 (Kuykendall) (Sickles G. M., *Proc. Soc. Exp. Biol. Med.* 102:742; Shafren D. et al *J. Virol* 1997, 71:4736; Hughes et al, *J. Gen Virol.* 1989, 70:2943; Schmidt, N. J., et al, *Proc. Soc. Exp. Biol. Med.*, 1961, 107:63. CVA21 (Kuykendall) is available from the American Type Culture Collection (ATCC) 10801 University Boulevard, Manassas, Va. 20110-2209, United States of America under Accession No. VR-850. Other preferred Coxsackie A-group viruses are also available from the ATCC and include CVA13 (Accession No. VR-171), CVA15 in particular G-9 (Accession No. VR-1021) and CVA18 (Accession No. VR-1024 and VR-176).

The Picornavirus may be naturally occurring or modified. The Picornavirus, is "naturally-occurring" when it can be isolated from a source in nature and has not been intentionally modified by humans in the laboratory. For example, the Picornavirus may be obtained from a "field source": that is, from a human patient.

The Picornavirus may be modified but still capable of lytically infecting a hematologic tumour or cancer.

Preferably, the Picornavirus used in a method or composition described herein will cause few or only minor clinical symptoms of viral infection in the recipient subject.

The Picornavirus may be a recombinant Picornavirus from two or more types of Picornaviruses with differing pathogenic phenotypes such that it contains different antigenic determinants thereby reducing or preventing an immune response by a mammal previously exposed to a Picornavirus subtype.

In methods of the invention, Picornavirus may be administered to a hematologic tumour or cancer in the individual subject. A combination of different serotypes and/or different strains and/or different species and/or different genera of Picornavirus, such as Coxsackievirus from different species of animal, may be used. If desired, the Picornavirus can be chemically or biochemically pretreated (e.g., by treatment with a protease, such as chymotrypsin or trypsin) prior to administration to the neoplasm. Such pretreatment removes the outer coat of the virus and may thereby result in better infectivity of the virus.

The Picornavirus may be administered or used in combination with other therapeutic agents. For example the Picornavirus may be administered with one or more different strain(s) or serotype(s) or species or genera of Picornavirus. The additional strain(s) or serotype(s) or species or genera of Picornavirus may have the same or different receptor requirements for cell infection as the Picornavirus of the invention.

As a further example the Picornavirus, or combination thereof, may be administered in combination with one or more agents capable of modulating or suppressing an immune response in the individual being treated. In this manner the natural immune response of the individual to viral infection may be altered, thereby preferably allowing a more efficacious viral infection and/or oncolytic and/or therapeutic outcome. Typically the agent capable of altering an immune response is an agent capable of suppressing an immune response. Agents capable of modulating or suppressing an immune response in an individual, such as a human individual, are described for example in The Merck Index, Thirteenth Edition, Merck & Co. Inc, Whitehouse Station, N.J. USA., the contents of which is incorporated herein by reference.

The Picornavirus, or combination thereof, may be used in combination with one or more chemotherapeutic agents, also referred to as antineoplastic agents. Antineoplastic agents are described for example in The Merck Index, Thirteenth Edition, Merck & Co. Inc, Whitehouse Station, N.J. USA. For example, the Picornavirus may be administered with chemotherapeutic agents such as: adriamycin, taxol, fluorouricil, melphalan, cisplatin, alpha interferon, COMP (cyclophosphamide, vincristine, methotrexate and prednisone), etoposide, mBACOD (methortrexate, bleomycin, doxorubicin, cyclophosphamide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include allylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar. The Picornavirus may be used in combination with one or more of bleomycin, vindesine, vincristine, dactamycin, procarbazine, lomustine or dacarbazine, for example for the treatment of melanoma. The Picornavirus may be used in combination with one or more of cisplatin and carboplatin, for example for the treatment of ovarian cancer. Further examples of chemotherapeutic agents that may be used in combination with the Picornavirus, for example for the treatment of breast cancer, include Cyclophosphamide (Cytoxan), methotrexate (Amethopterin, Mexate, Folex), and fluorouracil (Fluorouracil, 5-FU, Adrucil) [abbreviated CMF]; Cyclophosphamide, doxorubicin (Adriamycin), and fluorouracil [abbreviated CAF]; Doxorubicin (Adriamycin) and cyclophosphamide [abbreviated AC]; Doxorubicin (Adriamycin) and cyclophosphamide with paclitaxel (Taxol); Doxorubicin (Adriamycin), followed by CMF; Cyclophosphamide, epirubicin (Ellence), and fluorouracil. Other chemotherapy drugs used for treating women with breast cancer, for example, include docetaxel (Taxotere), vinorelbine (Navelbine), gemcitabine (Gemzar), and capecitabine (Xeloda).

It will be appreciated that the Picornavirus or combination thereof may be used in combination with known therapies for treatment of hematologic cancer, such as treatment of myeloma with thalidomide, proteasome inhibitor and arsenic trioxide.

It will be appreciated that use or administration of the Picornavirus "in combination" with one or more additional agents, such as one or more additional Picornaviruses, one or more agents capable of modulating or stimulating an immune response, or one or more antineoplastic agents, means use or administration in any manner in which the Picornavirus and additional agent(s) have therapeutic effect, such as an overlapping temporal effect. The members of the combination may be administered simultaneously or individually in any order that provides a desired therapeutic effect. When contemplated for combination therapy the Picornavirus and additional agent(s) may be in physical admixture or supplied separately, such as in kit form with or without instructions for administration. Kits according to the present invention may also include other components as required or as desired to conduct the methods of the present invention, such as buffers and/or diluents. The kits typically include containers for housing the various components and instructions for using the kit components in the methods of the present invention.

It will be appreciated that pharmaceutical compositions of the invention include compositions of the Picornavirus in physical admixture with one or more additional therapeutic agent(s), as well as compositions comprising a Picornavirus as the only therapeutically active agent.

The Picornavirus may be administered in combination with an effective amount of a probiotic agent. Probiotic agents may include, but are not limited to *Lactobacillus acidophilus, L. gasseri, L. confusus, Streptococcus thermophilus, Bifidobacterium breve*, and *B. longum*.

The haematological cancers—such as leukemia, lymphoma and myeloma—are cancers arising from bone marrow cells or lymphoid tissue. The haematological cancers can grow as solid tumours or separated cells in which case they occur in the blood as leukemia's.

Usually, at least some, of the cells of the hematologic cancer express ICAM-1 and/or DAF. Usually at least some of the cells of the hematologic cancer over-express ICAM-1 and/or DAF compared to non-malignant cells. Hematologic tumours or cancers that are particularly susceptible to treatment by the methods of the present invention include leukemia, multiple myeloma, Hodgkin's disease, non-Hodgkin's disease, Myelodysplasia, and lymphoma. Examples of leukemia include, but are not limited to chronic myelogenous leukemia, acute lymphocytic leukemia (ALL), chronic and lymphocytic leukaemia (CLL).

The Picornavirus is typically administered in a physiologically acceptable carrier or vehicle, such as phosphate-buffered saline, to the hematologic cancer. "Administration to a hematologic cancer" indicates that the Picornavirus is administered in a manner so that it contacts the cells of the hematologic cancer. The route by which the Picornavirus is administered, as well as the formulation, carrier or vehicle, will depend on the location as well as the type of the neoplasm. A wide variety of administration routes can be employed. For example, for a solid neoplasm that is accessible, the Picornavirus can be administered by injection directly to the neoplasm. For a hematopoietic neoplasm, for example, the Picornavirus may typically be administered intravenously or intravascularly. For examples intravenous delivery may be administered via single or multiple bolus dose injections or via slow infusion into the venous system for example using a drip. For neoplasms that are not easily accessible within the body, such as metastases or brain tumors, the Picornavirus is administered in a manner such that it can be transported systemically through the body of the mammal and thereby reach the neoplasm (e.g., intrathecally, intravenously or intramuscularly). Alternatively, the Picornavirus can be administered directly to a single solid neoplasm, where it then is carried systemically through the body to metastases. The Picornavirus may also be administered subcutaneously, intraperitoneally, topically, orally, rectally, vaginally, nasally or by inhalation spray.

In general, suitable compositions may be prepared according to methods which are known to those of ordinary skill in the art and accordingly may include a pharmaceutically acceptable carrier, diluent and/or adjuvant.

The compositions may be administered by standard routes. In general, the compositions may be administered by the parenteral (e.g., intravenous, intraspinal, subcutaneous or intramuscular), oral or topical route. More preferably administration is by the parenteral route.

The carriers, diluents and adjuvants must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; gum tragacanth or gum acacia, and petroleum jelly. Typically, the carrier or carriers will form from 10% to 99.9% by weight of the compositions.

The compositions may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranoasal inhalation or oral inhalation in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Where multiple administrations of Picornavirus are desired a different virus may be administered each time to avoid or minimise the effect of any immune response to a previously administered virus, and a course of treatment may extend for one to two weeks or more, such as one to two months or more, as may be determined by the attending physician. Most preferably, virus to which the mammal has not previously been exposed or to which the mammal generates a relatively minor immune response as may be determined by standard techniques may be administered.

A wide variety of administration routes may be employed. For example, for a hematologic cancer, the route of administration may be intravenously, intratumorally, intraperitoneally, intramuscularly, intraocularly, subcutaneously, orally, topically or by ex vivo purging of malignant cells within auto grafts prior to autologous stem cell transplantation.

The Picornavirus is administered in an amount that is sufficient to treat the hematologic cancer (e.g., an "effective amount"). A hematologic cancer is "treated" when administration of Picornavirus to cells of the cancer effects oncolysis of at least some of the cancer cells, resulting in a reduction in the degree of the cancer, or preferably in a complete elimination of the cancer. The reduction in the degree of the cancer, or preferably elimination of the cancer, is generally caused by lysis of hematologic cancer cells ("oncolysis") by the Picornavirus.

The effective amount will be determined on an individual basis and may be based, at least in part, on consideration of the type of Picornavirus; the individual's size, age, gender; and the type, extent and other characteristics of the hematologic cancer. For example, for treatment of a human, about $10^2$ to about $10^{10}$ plaque forming units (PFU) of Picornavirus, may be used, depending on specific circumstances such as the type, size and extent of cancer present. For example, the inoculant may contain greater than about $10^5$ PFU, for example between about $10^5$ to about $10^6$ PFU or between about $10^6$ to about $10^7$ PFU or between about $10^7$ to about $10^8$ PFU. As a further example the range of viral dose may be between about 0.01 to about 1000 infectious viral units per cell, for example from about 0.01 to about 0.1 infectious viral units per cell, or from about 0.1 to about 1 infectious viral units per cell, or from about 1 to about 10 infectious viral units per cell, or from about 10 to about 100 infectious viral units per cell, or from about 100 to about 1000 infectious viral units per cell.

The Picornavirus, may be administered in a single dose, or multiple doses (i.e., more than one dose). The multiple doses may be administered concurrently, or consecutively (e.g., over a period of days or weeks). Typically, in therapeutic applications the treatment would be for the duration of the disease condition, for example at least until the hematologic cancer was no longer detectable by conventional means. It is also contemplated that it may be desirable to continue treatment for a period beyond the presence of detectable cancer, for example where the treating physician suspects that undetectable neoplasms may be present. The Picornavirus may also be administered to more than one hematologic cancer in the same individual.

It will also be appreciated that the Picornavirus may be indirectly administered by using the RNA genome or a complementary DNA copy of the genome or a sufficient portion thereof to permit generation of a lytic response in virus-infected cancer cells. When administered, the Picornavirus will still be able to replicate in the cell and cause the desired lytic infection and killing.

Typically, the patient will be treated with an initial dose of the virus and subsequently monitored for a suitable period of time before a decision is made to administer further virus to the patient pending factors such as the response of the patient to the initial administration of the virus and the degree of viral infection and malignant cell death resulting from the initial treatment.

Desirably, an individual will be treated with the virus over a period of time at predetermined intervals. The intervals may be daily or range from 24 hours up to 72 hours or more, such as weekly or monthly, as determined appropriate in each circumstance. The same or a different virus may be administered each time, for example to avoid or minimise the effect of any immune response to a previously administered or encountered virus, and a course of treatment may extend for one to two weeks or more as may be determined by the attending physician. Most preferably, virus to which the individual has not previously been exposed or to which the individual generates a relatively minor immune response as may be determined by standard techniques will be administered. Alternatively and where desired administration of virus may be in combination with an immune-modulating agent for example where desired to reduce an immune response of a recipient to administered virus.

While readily available known viruses may be suitably employed in a method of the invention, a virus modified or engineered using conventional techniques may also be utilised. For instance, a virus may be modified to employ additional cell adhesion molecules as cell receptors. For example, Coxsackievirus A21 may be modified using site-directed mutagenesis so that the peptide motif "RGD" is expressed on the viral caspid surface as is the case with Coxsackievirus A9 (CVA-9). The RGD motif is recognised by all the $\alpha_v$ integrin heterodimers and this capsid modification may for instance allow the virus to bind the integrin $\alpha_v\beta_3$, a cell adhesion molecule which has been shown to be up-regulated in combination with ICAM-1 on the surface of malignant melanoma lesions leading to enhanced uptake of the virus via interaction with the integrin molecule or subsequent interaction with ICAM-1. Alternatively, the virus may be modified to recognise a selectin such as E-selectin or to target NF-κB signalling pathways.

The virus may be modified or selected to recognise alternative molecules for cell entry. Methods for such modification and selection are described in applicant's co-pending application PCT/AU2005/000048 (US 2008/0057036) entitled "Modified oncolytic viruses", the contents of which are incorporated herein by reference. For example, PCT/AU2005/000048 discloses an isolated selected Picornavirus capable of lytically infecting or inducing apoptosis in a cell substantially in the absence of intercellular adhesion molecule-1 (ICAM-1), such as through decay-accelerating factor (DAF) on the cell.

EXAMPLES

The invention will now be described in greater detail by reference to specific examples, which should not be construed as in any way limiting the scope of the invention.

Materials and Methods

Cells and Viruses

A prototype strain of Coxsackie A virus CVA21 (Kuykendall strain) was obtained from Dr M. Kennett, Enterorespiratory Laboratory, Fairfield Hospital, Melbourne, Victoria, Australia. CVA21 was double plaque purified and grown in ICAM-1 expressing melanoma cells (SK-Mel-28). Viruses were laboratory stock strains of CVA21, CVA18, CVA15 and CVA13. These prototype strains of Coxsackie A viruses CVA13 (Flores), CVA15 (G-9), CVA18 (G-13), and CVA21 (Kuykendall) were also obtained from Dr M. Kennett. Originally, CVA13, CVA15, and CVA18 were propagated in HeLa-B cells, while CVA21 Kuykendall was propagated in RD-ICAM-1 cells. Working laboratory stocks of these viruses were then prepared from these stocks in SK-Mel-28 cells.

SK-Mel-28 cells were a gift from Dr P. Hersey, Oncology, Mater Hospital, Waratah, New South Wales, Australia. U266, RPMI-8226 and NCI-H929 multiple myeloma cell lines were obtained from Dr L. Lincz, Hematology, Mater Misericordiae Hospital (Hunter Hematology Research Group), Edith Street, Waratah, New South Wales, 2298, Australia. Additional cell lines B cell lymphoma cell line SCOTT, B prolymphocytic leukemia cell line JVM13, acute promyelocytic leukemia (APML) cell lines NB4 and HL-60, and monocytic leukemia cell line U937 were also obtained from Dr L. Lincz. SK-Mel-28 cells were maintained in DMEM containing 10% fetal calf serum (FCS), while U266, RPMI-8226, NCI-H929, SCOTT, JVM13, NB4, HL-60 and U937 cells were cultured in RPMI containing 10% FCS. All cell lines were maintained at 37° C. with a 5% $CO_2$ environment. Normal peripheral blood mononuclear cells (PBMCs) from healthy donors were isolated by layering whole blood samples on Ficoll-Hypaque Plus gradients in a 4:1 ratio, before centrifugation at 400×g for 35 min. The interlayer was collected, resuspended in phosphate buffered saline (PBS) and then washed twice in PBS before further use.

Primary Tumor Cells

All procedures were approved at the University of Newcastle Human Care and Ethics Committee (Newcastle, NSW, Australia) and the Hunter Area Health Service Human Care and Ethics Committee (Newcastle, NSW, Australia). Primary tumor cells were obtained from patients undergoing routine bone marrow investigation for multiple myeloma diagnosis. Bone marrow aspirates were collected from 19 patients as indicated in Table 1.

TABLE 1

| Patient ID | Date of sample | Sex | Age | Status |
|---|---|---|---|---|
| 1 | Jun. 21, 2004 | M | 55 | Relapsed |
| 2 | Jun. 30, 2004 | M | 76 | Relapsed |
| 3 | Jul. 20, 2004 | F | 44 | Persistent |
| 4 | Jul. 28, 2004 | F | 69 | MGUS |
| 5 | Jul. 28, 2004 | M | 80 | MM diagnostic sample |
| 6 | Aug. 11, 2004 | M | 85 | MGUS |
| 7 | Sep. 10, 2004 | F | 77 | Diagnosis |
| 8 | Feb. 14, 2005 | M | 44 | diagnosis |
| 9 | Feb. 16, 2005 | M | 46 | pre-transplant |
| 10 | Feb. 23, 2005 | F | 75 | dry tap |
| 11 | Feb. 28, 2005 | M | 55 | PR |
| 12 | Mar. 2, 2005 | M | 70 | Relapsed |
| 13 | Apr. 13, 2005 | M | 57 | PR |
| 14 | May 11, 2005 | F | 80 | MGUS |
| 15 | Jun. 1, 2005 | F | 72 | Waldenstroms Macroglubulinemia |
| 16 | Jun. 1, 2005 | F | 60 | MM diagnosis |
| 17 | Aug. 3, 2005 | F | 67 | MGUS |
| 18 | Aug. 10, 2005 | M | 66 | Plasmacytoma |
| 19 | Aug. 10, 2005 | F | 72 | MGUS |

"PR" partial remission; "dry tap" means no marrow (bone particles). All patients gave informed consent. Single cell suspensions were obtained from bone marrow samples by overlaying the sample on Lymphoprep solution (Nycomed, Oslo, Norway) in a ratio of 2:1, and centrifuged for 30 min at 400×g. The mononuclear cell layer was collected, washed twice in PBS, and resuspended in RPMI containing 5% FCS prior to use in further experiments.

Antibodies

Commercially available anti-CD54 antibody conjugated with fluorescein-isothiocyanate (FITC), (Immunotech Coulter, Marseilles, France) directed against the N-terminal domain of ICAM-1 (Berendt A R, et al. *Cell*. 1992; 68:71-81), was used for staining surface expressed ICAM-1. Anti-DAF IH4 mAb was obtained from Dr B. Loveland, Austin Research Institute, Heidelberg, Victoria, Australia. The anti-CD138-FITC mAb (Serotec, Oxford, UK) was specific for the plasma cell antigen Syndecan-1. Another commercially available anti-CD138 antibody conjugated with phycoerythrin (PE) was obtained from Miltenyl Biotec, Calif. USA.

Flow Cytometry

ICAM-1 and DAF surface expression on multiple myeloma cell lines and other hematologic cancer cell lines B cell lymphoma, B prolymphocytic leukemia, acute promyelocytic leukemia (APML) and monocytic leukemia were analyzed by two-colour flow cytometry. Briefly, dispersed cells ($1 \times 10^6$) were incubated on ice with the directly conjugated anti-CD54-FITC mAb (5 µg/ml diluted in phosphate buffered saline (PBS)) for 20 min. Cells were then washed with PBS, pelleted at 1000×g for 5 min before dual labeling with the anti-DAF IH4 mAb (5 µg/ml in PBS) for 20 min on ice. The cells were washed with PBS and resuspended in 100 µl of the secondary antibody solution; R-phycoerythrin-conjugated F(ab')$_2$ fragment of goat anti-mouse immunoglobulin diluted 1:100 in PBS (DAKO A/S, Denmark) and incubated on ice for 20 min. For each cell line, staining with the appropriate conjugate control antibodies was also carried out alongside. Cells were washed and pelleted as above, resuspended in PBS and analyzed for ICAM-1 and DAF expression using a FACStar analyzer (Becton Dickenson, Sydney, Australia).

Viral Lytic Infection and Cell Viability Assay

Multiple myeloma cell lines RPMI-8226, U266 and NCI-H929 were cultured in 6-well plates with or without CVA21 for 48 h. Normal human peripheral blood mononuclear cells obtained from a healthy volunteer, were used as a control. The multiplicity of infection (MOI) was approximately 5 $TCID_{50}$ per cell for each culture. The cytopathic effect (CPE) was evaluated 48 h post CVA21 infection using a trypan blue viability stain. Due to the affinity of trypan blue for proteins secreted into the culture supernatant by the multiple myeloma cell lines, the culture supernatant was first removed by slow aspiration through a blunted 26-gauge needle prior to staining. The remaining cells were stained with a 0.4% trypan blue solution for 5 min. Photographs were taken at a magnification of ×100.

In Vitro Growth Inhibition Assay

A modified version of a microculture tetrazolium assay (Alley M C, et al. *Cancer Res*. 1988; 48:589-601), was used to study the effect of increasing CVA21 concentrations on the growth of multiple myeloma cell lines. In brief, multiple myeloma cells were harvested from exponential-phase maintenance cultures, and dispensed within replicate 96-well culture plates in 100 µl volumes ($1 \times 10^5$ cells/well). 100 µl of culture medium, or culture medium containing virus ($2 \times 10^{-5}$-20 $TCID_{50}$/cell) was dispensed in the appropriate wells. For comparing the growth inhibition of other Coxsackie A viruses (CVA13, CVA15 and CVA18) with CVA21, 10-fold serial dilutions ranging from $1 \times 10^4$ to 100 $TCID_{50}$/cell were used. Wells containing no cells were utilized for the media alone or virus solution alone blank "background" determinations.

Culture plates were incubated for 2 days at 37° C. prior to the addition of the MTT reagent (Sigma Chemicals, Sydney, New South Wales, Australia). The MTT stock solution was prepared as a 5 mg MTT/ml PBS solution and sterile filtered with 0.2 µm filter units and stored at 4° C. To determine the level of growth inhibition following the 2 day incubation, 20 µl of the stock MTT solution was added to each culture well, and incubated at 37° C. for a further 4 h.

Following incubation, the cell supernatant was removed from wells by slow aspiration through a blunted 26-gauge needle and replaced with 150 µl of DMSO. The formazan crystals were thoroughly solubilized by gentle shaking at room temperature (RT), and the absorbance of each well measured using an ELISA plate reader (Flow Laboratories, McLean, Va. USA) at 540 nm. Subsequently cell line growth inhibition was expressed in terms of mean absorbance units as a percentage of control absorbance readings following subtraction of mean "background" absorbance.

Virus Yield and Endpoint Titration

Following the determination of CVA21 CPE in the three myeloma cell lines, an experiment to determine the yield of infectious virus particles produced during infection was performed in U266, RPMI-8226, NCI-H929 cells and PBMCs. Approximately $3 \times 10^6$ cells from each cell line were infected with a MOI of 1 $TCID_{50}$/cell. The CVA21 inoculated U266, RPMI-8226, NCI-H929 cells and PBMCs were washed twice with PBS and resuspended in 600 µl of RPMI before being each divided into three 200 µl aliquots (~$1 \times 10^6$ cells/tube). The tubes were incubated at 37° C., with one aliquot from each of the cell lines collected and the cells harvested by three consecutive freeze-thaw cycles at times 0, 12, 24 and 48 h. The viral yield in each of the cell lysates were assessed by an endpoint titration assay in SK-Mel-28 cells. Results are presented in FIG. 4.

Briefly, for the endpoint titration assay, confluent monolayers of SK-Mel-28 cells in 96 well tissue culture plates were inoculated with 10-fold serial viral dilutions (100 µl/well in quadruplicate) and incubated at 37° C. in a 5% $CO_2$ environment for 48 h. Cell survival was quantitated by incubation with crystal violet/methanol solution (0.1% crystal violet, 20% methanol, 4.0% formaldehyde in PBS) (100 µl/well) for 24 h and following three washes with distilled water, the relative absorbance of individual wells was read on a multiscan enzyme-linked immunosorbent assay plate reader (Flow Laboratories, McLean, Va. USA) at 540 nm. Fifty percent viral end point titers were calculated using the SpearmanKarber method; by scoring wells as positive if the absorbance values were less than the mean minus three standard deviations (SD) of the control no virus wells.

An experiment to determine the yield of infectious virus particles (CVA21) produced during infection was also performed in selected hematologic cancer cell lines, namely MM cell line RPMI-8226, monocytic leukemia cell line U937 and acute promyelocytic leukemia (APML) cell line HL-60. The method was similar to that described above, although cells were infected with CVA21 at $10TCID_{50}$/cell, with the virus allowed to bind for 30 min at 37° C. before being washed and then placed in fresh media (RPMI 10% FCS). Cells and supernatant were harvested at 0, 24 and 48 h post infection and the amount of virus was determined by endpoint titration on monolayers of SK-MEL-28 cells. Results are presented in FIG. 13.

Viral Growth Rates

To investigate the replication kinetics of CVA21 in the three myeloma cell lines, tubes containing $1 \times 10^6$ of U266, RPMI-8226 or NCI-H929 cells were infected with 100 µl viral aliquots containing approximately $3 \times 10^6$ $TCID_{50}$ of CVA21 (MOI-3 $TCID_{50}$/cell). The tubes were gently shaken for 30 min at room temperature, the cells were then washed five times each with 5 ml of RPMI and the cells resuspended in 1 ml of RPMI containing 1% FCS. Each tube of CVA21 inoculated cells was then divided into 9 separate 100 µl aliquots (~$1 \times 10^5$ cells/tube) for collection at the appropriate time points. Tubes were incubated at 37° C. for the duration of the experiment. Synchronized infection was interrupted at time intervals of 0, 2, 4, 6, 8, 10, 12, 24 and 48 hours, one aliquot from each of the cell lines tested was collected at each time point and cells were lysed by three consecutive freeze-thaw cycles, subjected to centrifugation at 10,000×g at room temperature for 5 min before the viral yield in the cell lysate was determined in an endpoint titration assay.

DNA Fragmentation Assay

The induction of apoptosis by CVA21 infection of MM cells was determined by the detection of genomic DNA fragmentation. MM cell lines RPMI-8226, U266 and NCI-H929 were cultured in six-well plates ($5×10^5$ cells/well) and either infected with CVA21 (MOI~10 $TCID_{50}$/cell) or left uninfected with media alone for 24 h at 37° C. prior to analysis. The cells were pelleted by centrifugation at 800 g for 5 min and then 500 µl of lysis buffer (5 mM Tris-HCl, 20 nM EDTA, 0.5% Triton X-100, pH 8.0) was added to the cell pellet and incubated on ice for 20 min. The lysate was centrifuged at 12,000 g for 20 min and the DNA was extracted from the supernatant using phenol: chloroform. The DNA was ethanol precipitated, washed in 70% ethanol and resuspended in 30 µl of TAE containing RNase (50 µg/ml). The DNA samples were incubated for 30 min at 37° C. before analysis by agarose gel electrophoresis. Fifteen microliters of the extracted DNA was mixed with 3 µl of loading buffer (0.25% Orange G, 40% glycerol in TAE) and then resolved on a 1.2% TAE agarose gel containing ethidium bromide. The gel was visualized under UV light and an image was captured digitally using the Gel Doc system (Bio-RAD, Regents Park, New South Wales, Australia).

Selective CVA21 Infection of Myeloma Cell Lines Co-Cultured with Normal Peripheral Blood Mononuclear Cells U266 and RPMI-8226 myeloma cells were each mixed with PBMCs in RPMI medium supplemented with 10% FCS to result in a final plasma cell concentration of 10%. Cell mixtures were treated with CVA21 (1 MOI per total cell population) or left untreated for 72 h. On day 3 of purging, samples from each mixture of cell populations were harvested in PBS, and intact cancer cell numbers were evaluated using flow cytometry following staining first with anti-CD138-FITC (10 µl/ml) for 30 min, and then propidium iodide (PI) (5 µg/ml) for 10 min. Cells were washed in 5 ml of PBS, and pelleted by centrifugation at 1000 g, before analysis on a FACStar analyzer (Becton Dickenson, Sydney, Australia). Cells that were no longer viable or intact were stained positive with propidium iodide ($PI^+$), while staining with anti-CD138-FITC was used to determine multiple myeloma cells ($CD138^+$) from normal PBMCs ($CD138^-$).

Ex Vivo Purging of Patient Bone Marrow Samples with CVA21

Primary tumor samples were obtained from two multiple myeloma patients who gave informed consent, and only surplus cells from bone marrow aspirates collected during routine diagnosis were used for this study. Firstly, ICAM-1 receptor levels were assessed for each clinical sample by the dual staining of primary tumor cells ($1×10^5$ cells) with anti-CD138-PE (10 µg/ml) and anti-ICAM-1-FITC antibodies (5 µg/ml) based on standard surface receptor staining protocols as described above. Growth inhibition/MTT assays were then performed on clinical samples infected with CVA21 in triplicate. Approximately $1×10^5$ cells (in RPMI containing 5% FCS) were then seeded into wells of a 96 well plate for the assessment of CVA21 oncolysis at 10-fold serial dilutions ranging from 0 to 16 $TCID_{50}$/cell. These cells were incubated for 48 h at 37° C. before analysis using the MTT assay.

Following the growth inhibition assay, single cell suspensions from clinical bone marrow samples ($1×10^6$ cells in RPMI containing 5% FCS) were seeded into each well of a six-well plate, and incubated with CVA21 at concentrations of 0, 2.75, 5.5 and 11 $TCID_{50}$/cell for 48 h. The cells were then harvested by gentle pipetting, and resuspended in 4 ml of PBS and washed once before proceeding with analysis for cell viability. The selectivity of CVA21 mediated oncolysis for MM cells was measured by flow cytometry using the cell viability dye propidium iodide (5 µg/ml) and the anti-CD138-FITC (10 µg/ml) antibody.

Additional clinical samples (total 19) as indicated in Table 1 were similarly assayed.

Results

MM Cells Express ICAM-1 and DAF

Figure 1:
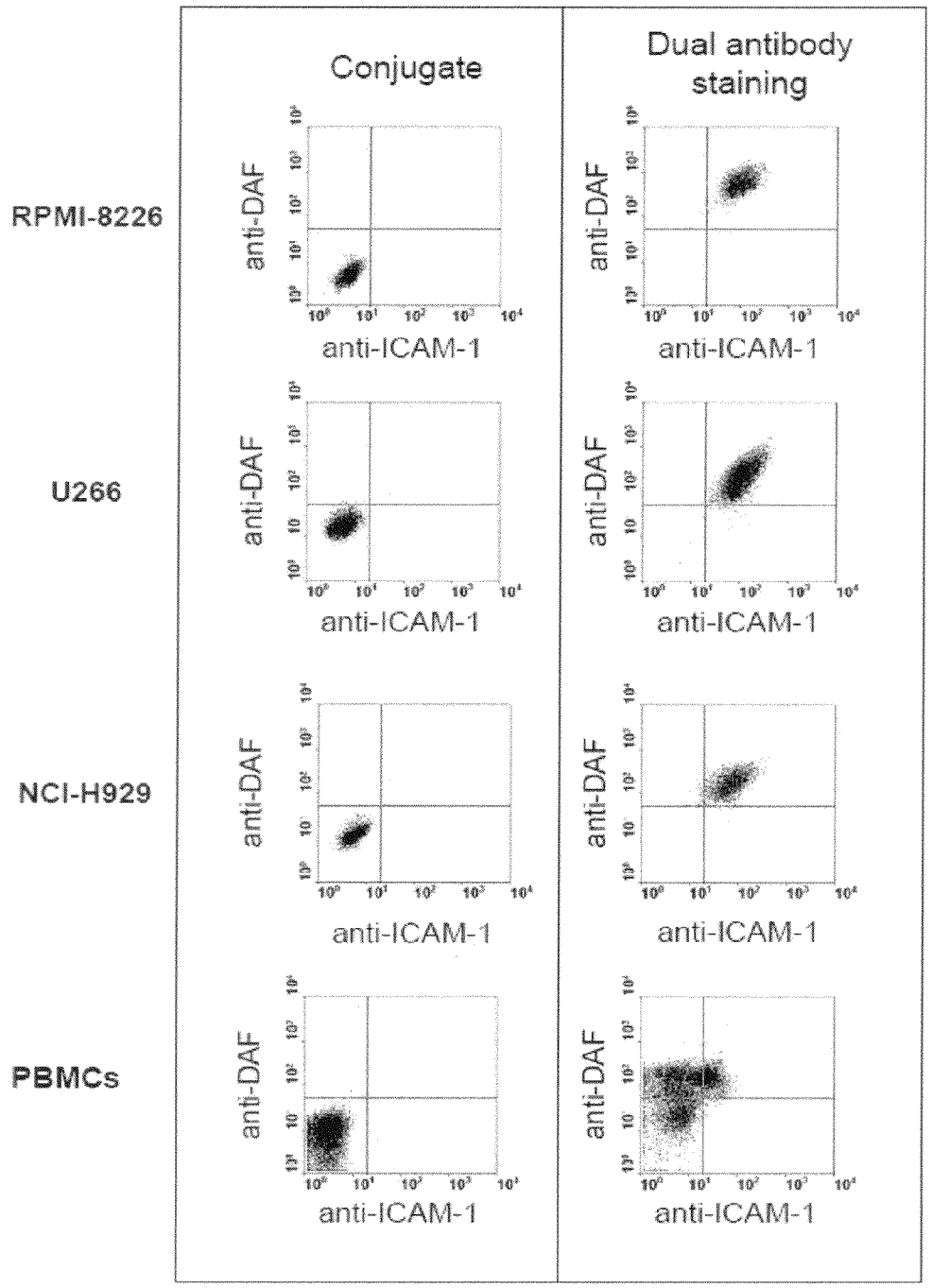
FIG. 1. Flow cytometric analysis of ICAM-1 and DAF on multiple myeloma cell lines.

Flow cytometry was used to assess the relative levels of CVA21 cell-entry receptors ICAM-1 and DAF on the surface of several MM cell lines. U266, RPMI-8226 and NCI-H929 cells were analyzed by flow cytometry after dual staining with anti-ICAM-1 and anti-DAF antibodies. Each of the three cell lines demonstrated elevated levels of both ICAM-1 and DAF, as highlighted by the stained cells in the upper right quadrant of each dot plot (FIG. 1) compared to the conjugate controls. Not all cells in the PBMC sample however displayed ICAM-1 surface expression, with a majority of cells staining negatively for ICAM-1. PBMCs however were positive for DAF expression, as seen in the upward shift of the PBMC population in the dual stained sample in contrast to the conjugate control, Expression of ICAM-1 and DAF in Hematologic Cancer Cell Lines In order to investigate further the potential susceptibility of hematologic cancers to Picornavirus infection and lysis the expression of the cell entry receptors ICAM-1 and DAF was demonstrated on a panel of representative cell lines. Flow cytometry was used to assess the relative levels of CVA21 cell-entry receptors ICAM-1 and DAF on the surface of B cell lymphoma cell line SCOTT, B prolymphocytic leukemia cell line JVM13, acute promyelocytic leukemia (APML) cell lines NB4 and HL-60, monocytic leukemia cell line U937 and multiple myeloma cell line H929 after dual staining with anti-ICAM-1 and anti-DAF antibodies. The B cell lymphoma cell line SCOTT, the B prolymphocytic leukemia cell line JVM13 and the MM cell line H929 demonstrated expression of both ICAM-1 and DAF, as highlighted by the stained cells in the upper right quadrant of each dot plot (FIGS. 11A and B) compared to the conjugate controls. Monocytic leukemia cell line U937 also demonstrated elevated levels of ICAM-1 and DAF although to a lesser extent. Whilst staining positively for DAF expression, the majority of cells in the acute promyelocytic leukemia (APML) cell lines NB4 and HL-60, stained negatively for ICAM-1.

MM Cells are Susceptible to Lytic Infection by CVA21.

To assess whether the ICAM-1 and DAF expressing multiple myeloma cells were susceptible to CVA21 oncolysis, cells were infected with CVA21 (MOI~5 $TCID_{50}$/cell) for 48 h at 37° C. Each of the multiple myeloma cell lines showed initial signs of CVA21 infection at 24 h. The maximal cytopathic effect of CVA21 in U266, RPMI-8226 and NCI-H929 cell lines was observed between 24-48 h post-infection as seen by the clumping and aggregation of the cells and the uptake of trypan blue (FIG. 2). Cytopathic effect in human peripheral blood mononuclear cells was minimal compared to the three multiple myeloma cell lines.

CVA21 Infection Inhibits Growth of MM Cells

The differential killing and growth inhibition of CVA21 on various multiple myeloma cell lines was examined in more detail using the MTT cell viability assay. Plated U266, RPMI-8226 and NCI-H929 cells were exposed to increasing concentrations of CVA21 for 48 h. The oncolytic effect of CVA21 was determined by MTT survival as a function of increasing doses of CVA21 FIG. 3 illustrates the growth inhibition profile and dose-dependent shoulder following CVA21 exposure. Each of the MM cell lines assayed were found to be sensitive, with RPMI-8226 and U266 cell lines revealing significant growth inhibition in response to low concentrations of CVA21. Normal PBMCs were inhibited in growth following exposure to high concentrations of virus, however even at 20 MOI there was an 80% survival of PBMCs compared to the MM cell lines which were each below 10% survival.

MM Cells Support the Propagation of Progeny CVA21

To determine the capacity of CVA21 infected MM cells to produce infectious progeny for further oncolytic effect, virus yields following CVA21 infection with U266, RPMI-8226, NCI-H929 and PBMCs were measured. At 24 and 48 h post infection, virus yields from the three myeloma cell lines show a dramatic increase in virus titer compared to the 0 h time point (FIG. 4). PBMCs however do not show an increase in CVA21 yield, providing evidence that CVA21 does not permissively replicate within normal human PBMCs. CVA21 was allowed to propagate in PBMCs to an extended period of 6 days without any CVA21 replication or increase in virus yield (data not shown).

When assayed under similar, although not identical conditions, monocytic leukemia cell line U937 and acute promyelocytic leukemia (APML) cell line HL-60 did not show an increase in CVA21 yield at either 24 or 48 h post infection, suggesting that CVA21 does not permissively replicate within either U937 or HL-60. (FIG. 13).

CVA21 has a Rapid Growth Rate in MM Cells

One advantage of virus therapy of malignant cells is the ability for infectious progeny virus to be produced that can further target surrounding malignant cells at local or even distant sites. Following the synchronous infection of the three multiple myeloma cell lines, complete cells and supernatant were collected at the indicated time points (FIG. 5). The replication of CVA21 within cancerous cell lines was found to be very rapid, and increases in viral titer from infected multiple myeloma cells were observed as soon as four hours post virus inoculation with CVA21. The one-step growth curve analysis of CVA21 in U266, RPMI-8226 and NCI-H929 cells demonstrated efficient viral replication to maximal titers between 8 and 12 h post infection.

CVA21 Induced Apoptosis in RPMI-8226 and NCI-H929 Cells

To determine whether CVA21 induces apoptosis of multiple myeloma cells during infection, CVA21 was incubated with either RPMI-8226, NCI-H929 or U266 cells at a MOI of approximately 10 $TCID_{50}$ per cell, and apoptosis assessed by a DNA fragmentation assay 24 h after infection. CVA21 induced DNA laddering characteristic of apoptosis (FIG. 6), in infected RPMI-8226 and NCI-H929 cells (lanes 2 and 4, respectively) but not in infected U266 cells (lane 6). DNA fragmentation was not observed in U266 cells treated with CVA21, indicating that CVA21 oncolysis in this cell line did not induce apoptosis. The results suggest that CVA21 is capable of inducing apoptosis in RPMI-8226 and NCI-H929 cells, but may be activating anti-apoptotic signalling pathways during the oncolysis of U266 myeloma cells. Lanes 1, 3 and 5 contained the DNA extracted from the mock-infected control cells.

Ex Vivo Purging of Myeloma Co-Cultures Containing Malignant and Nonmalignant Cells The specificity of CVA21 for oncolysis of multiple myeloma cells and not normal cells was studied by mixing multiple myeloma cells with normal human peripheral blood mononuclear cells to result in a tumor burden of approximately 10%, and purging with CVA21 for 3 days. By staining with anti-CD138-FITC and PI, viable and non-viable populations of normal PBMCs and multiple myeloma cells could be distinguished. As seen in FIG. 7 ("no virus"), prior to infection with CVA21, populations of viable RPMI-8226 or U266 cells ($CD138^+/PI^-$) can be seen in the lower right quadrants of the flow cytometry dot plot. Following purging of RPMI-8226 or U266 co-cultures with CVA21 for 3 days at a MOI of 1 $TCID_{50}$/cell, less than 0.26% and 0.51% of viable myeloma cells, respectively, are remaining. CVA21 was able to purge approximately 98% of RPMI-8226 and approximately 95.7% of U266 cells from co-cultures. The viable lymphocyte populations are shown in the bottom left hand quadrants, and stain negatively with CD138 and PI. Following infection with virus, these populations remain relatively unchanged even after 3 days of exposure to CVA21.

Purging of Multiple Myeloma Cells from Clinical Bone Marrow Samples

After demonstrating the effective oncolysis of several multiple myeloma cell lines in vitro, the ex vivo purging of cancerous cells from two primary multiple myeloma bone marrow samples was confirmed. Bone marrow aspirates from two patients undergoing routine diagnosis, were processed into single cell suspensions. Cells were first stained with anti-CD133 and anti-ICAM-1 antibodies to determine the surface expression of ICAM-1 on multiple myeloma cells. A significant correlation between myeloma status ($CD138^+$) and ICAM-1 expression was found in both clinical samples tested with results from one of the clinical samples depicted in FIG. 1A. In clinical sample #001, approximately 37% of total cells were multiple myeloma plasma cells and expressed both the CD138 marker and ICAM-1. A similar proportion of myeloma cells were found in the second patient with approximately 41% of cells staining with both CD138 and ICAM-1 (data not shown).

Figure 8B:
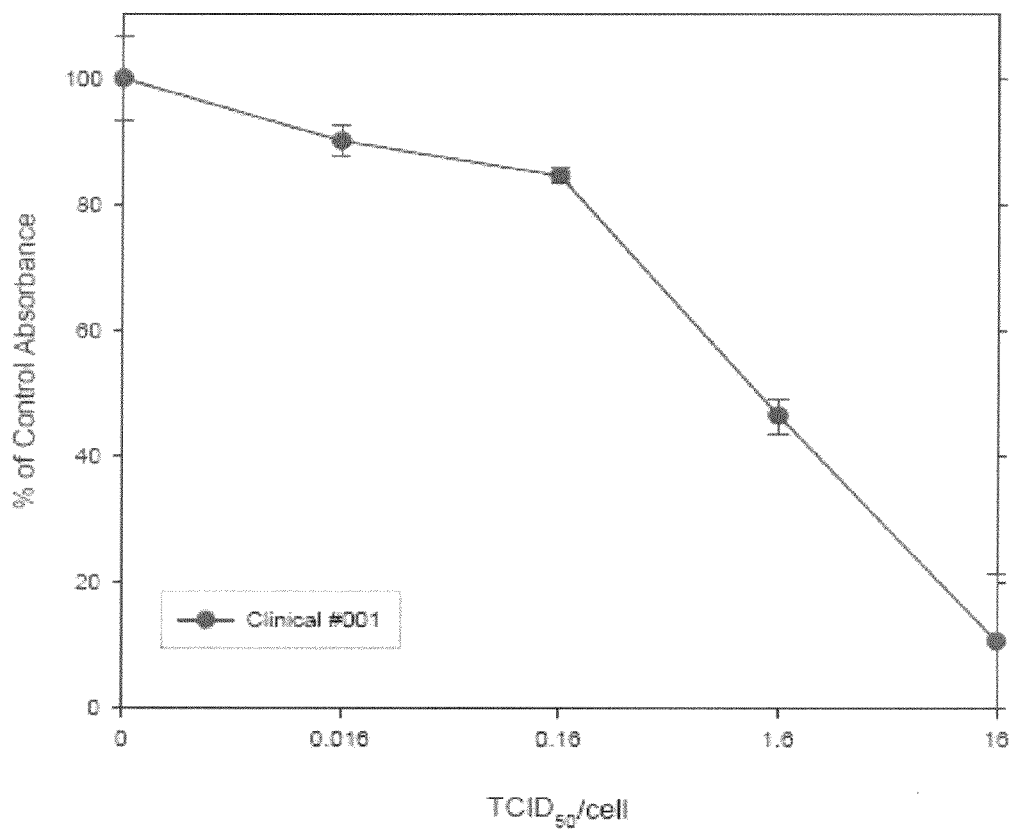

Results from the MTT assays on patient clinical samples confirmed that CVA21 treatment effectively inhibited myeloma cell growth in a dose dependant manner following 48 h incubation with different concentrations of virus. Following the challenge of primary tumor cells (sample #001) with varying concentrations of CVA21, the percentage of proliferating cells steadily decreased with higher inputs of virus (FIG. 8B). As the primary tumor samples also contained a proportion of non-malignant cells, the specificity of CVA21 to specifically infect MM cells was yet to be determined.

Figure 9A:
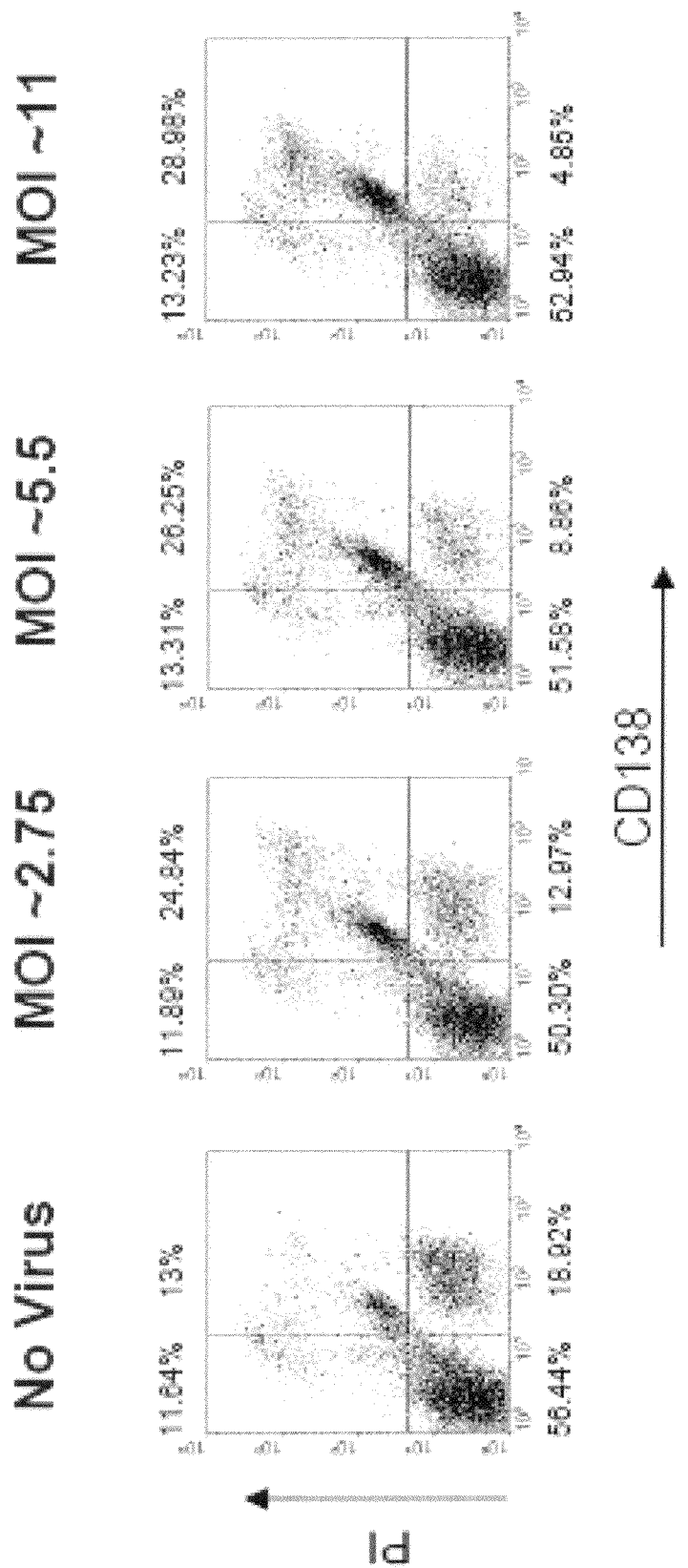
Figure 9B:
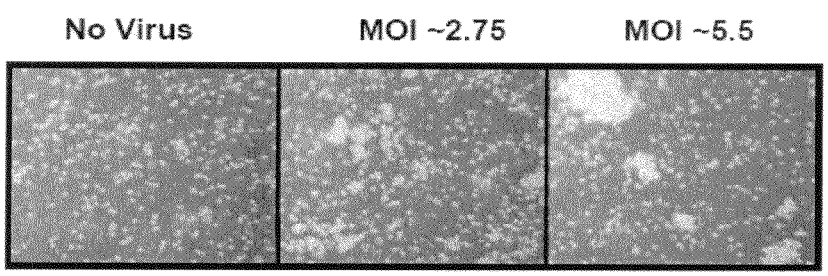
Figure 9C:
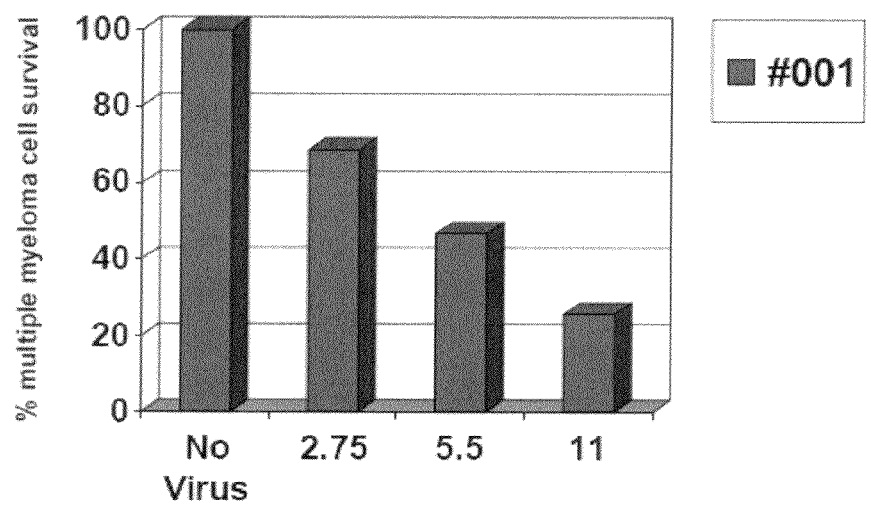

To test whether CVA21 was selective in mediating specific lysis of multiple myeloma cells, and not normal cells, primary tumor samples were infected with varying concentrations of CVA21 for 48 h and then analyzed by staining with anti-CD138 antibodies and propidium iodide. Using flow cytometry, the viability of $CD138^+$ and $CD138^-$ cells was determined (FIG. 9A) with cytopathic effect observed at three concentrations of CVA21 infection at 48 h (FIG. 9B). Tumor cells from clinical sample #001 incubated for 48 h with CVA21 at concentrations of 0, 2.75, 5.5 and 11 $TCID_{50}$/cell revealed that the percentage of live myeloma cells ($CD138^+/PI^-$) counted by flow cytometry, decreased with increasing input of virus (FIG. 9A). Primary tumor cells infected with CVA21 at 11 $TCID_{50}$/cell, led to a 74% reduction in the percentage of malignant myeloma cells detected. In this primary tumor sample, the number of non-viable myeloma cells ($CD138^+/PI^+$) steadily increased and corresponded to the decrease in viable myeloma cells ($CD138^+/PI^-$).

These results were also reflected in the other clinical sample, and following a longer incubation with CVA21, a maximum of 90% reduction in viable tumor cells was achieved (data not shown). Even with no virus treatment, both clinical samples had low levels of nonviable cells present, and more importantly the level of non-viable CD138⁻ cells did not increase substantially following virus treatment in the clinical samples tested. Another factor to consider is that the ex vivo culture of these cells for 48 h may have also contributed to low levels of cell death, as observed in the no virus controls. The percentage of viable multiple myeloma cells from clinical sample #001 remaining follow treatment with different concentrations of CVA21 is summarized from the flow cytometry data and shown in FIG. 9C.

To further assess the clinical utility of CVA21 as an ex vivo purging agent, additional BM aspirates were investigated. Results for BM aspirates from 5 patients with MM and 2 with MGUS infected with CVA21 at concentrations of approximately 3 and 10 MOI are presented in FIG. 10B(i). Cumulative results for a total of 19 clinical samples with a range of conditions (Table 1) are shown in FIG. 10B(ii). Populations of CD138⁺ cells from all clinical samples tested expressed ICAM-1; a representative dot plot from patient sample #006 is shown (FIG. 10A). CVA21 had a potent oncolytic purging effect in all 7 clinical samples tested following a single treatment with virus, as shown by the substantial reduction in viable CD138⁺ cells, with a maximum of 97.2% elimination of MM cells in sample #008 (FIGS. 10B(i) and 10E). The level of viable CD138⁻ normal cells did not decrease substantially following virus treatment (FIG. 10D). More importantly, the progenitor cells in this fraction retained the capacity to support haemopoiesis. FIG. 10C reveals that viable progenitor stem cells can be cultured following treatment of primary samples with CVA21; the average numbers of CFU-GM colonies from three patient samples are shown. Compared to the mock infected control samples, the number of CFU-GM colonies were 57-70% lower in the virus treatment groups.

Susceptibility of Hematologic Cancer Cell Lines to CVA13, CVA15 and CVA18

Other Coxsackie A viruses that use ICAM-1 to infect and destroy cells, (such as CVA13, CVA15 and CVA18) were also capable of inhibiting multiple myeloma cell growth. Using RPMI-8226 cells as a representative multiple myeloma cell line, CVA13, CVA15 and CVA18 treatment of these cells demonstrated similar anti-tumoral effects as that of CVA21 at concentrations of 0.1 to 100 TCID₅₀/ml (FIG. 12A). The effect of CVA13, CVA15, CVA18 and CVA21 were less consistent when assayed on non-multiple myeloma cancer cells U937 and HL-60 (FIGS. 12B and C). Although some growth inhibition was observed with each of the viruses on U937 and HL-60 cells, detailed investigation into the yields of CVA21 growth following infection of these cells suggest that the cancer cell lines U937 and HL-60 are not able to support viral replication and therefore may not be ideal candidates for viral therapy (FIG. 13).

Discussion

Coxsackievirus A21 is a novel oncolytic agent that was first shown to be an effective anti-tumor agent against malignant melanoma CVA21 is a picornavirus commonly associated with mild upper respiratory tract infections, and is not known to cause serious disease in humans (Rueckert R. R. Picornaviridae: The Viruses and Their Replication. In: Fields B N, Knipe D M, Howley P M, eds. *Fields Virology*. Vol 1. Philadelphia: Lippincott-Raven; 1996:609-645). These results demonstrate that CVA21 is a potent oncolytic agent against multiple myeloma following in vitro testing of several MM cell lines. This conclusion is supported by the observed cytopathic effect of CVA21 on MM cell lines (FIG. 2), and by the significant growth inhibition/cytotoxicity of CVA21 on MM cells as verified via MTT assays (FIG. 3).

The data reported herein also demonstrate that other Picornaviruses, exemplified by CVA13, CVA15 and CVA18, are potent oncolytic agents against MM cells (FIG. 12).

This effect is not limited to MM cells as demonstrated herein by the responsiveness of the monocytic leukemia cell line U937 to CVA13, CVA15, CVA18 and CVA21, although with an apparent greater dose dependency than MM cells (FIG. 12B).

Using flow cytometry, multiple myeloma cell lines U266, RPMI-8226 and NCI-H929 were confirmed to express high levels of the CVA21 viral-entry receptors ICAM-1 and DAF (FIG. 1), these two molecules being determinants of CVA21 oncolytic selectivity and efficacy.

Expression of ICAM-1 and DAF in cell lines established from additional hematologic cancers was also demonstrated herein, emphasising the broad potential of treatment of hematologic cancers with Picornaviruses. As shown in FIG. 11 the B cell lymphoma cell line SCOTT and the B prolymphocytic leukemia cell line JVM13 both demonstrated expression of both ICAM-1 and DAF. Monocytic leukemia cell line U937 also demonstrated elevated levels of ICAM-1 and DAF although to a lesser extent. Consistent with the apparent absence of detectable susceptibility of the acute promyelocytic leukemia (APML) cell line HL-60 to CVA21, the majority of HL-60 cells stained negatively for ICAM-1.

B cell lymphoma cell line SCOTT and B prolymphocytic leukemia cell line JVM13 were very slow growing under the culture conditions used herein. As a consequence, it was not possible to directly demonstrate the efficacy of oncolytic infection of either of these cell lines with CVA as was demonstrated for various other hematologic cancer cell lines. In view of the demonstrated expression of ICAM-1 and DAF on each of these cell lines, however, the applicant believes that each of B cell lymphoma and B prolymphocytic leukemia will be susceptable to the methods of the invention.

High levels of ICAM-1 expression by MM cells have been well documented in the literature, leading to the generation of several proposals for anti-ICAM-1 mAb therapies as potential treatments for MM (van de Stolpe A, van der Saag P T. *Journal of Molecular Medicine*. 1996; 74:13-33; Huang Y W, et al. *Cancer Res*. 1995; 55:610-616). The reason for this high level of ICAM-1 expression in MM cells can be explained by the constitutive activation of the transcription factor NF-κB in MM cells (Hideshima T, et al. *J Biol Chem*. 2002; 277:16639-16647).

NF-κB is a cell survival factor related to MM pathogenesis and drug resistance, and is an important regulator of adhesion molecule expression in MM cells (Chauhan D, et al. *Blood*. 1996; 87:1104-1112). The 5' promoter region of the ICAM-1 gene contains several κB enhancer elements and represents one of the most important transcription-regulatory elements in the regulation of ICAM-1 expression. The activation of NF-κB in MM cells and resultant up-regulation of adhesion molecules such as ICAM-1 have been shown to increase MM cell binding to bone marrow stromal cells (BMSC) (Hideshima T, et al. *Oncogene*. 2001; 20:4519-4527). It has also been confirmed that the adhesion of MM cells to BMSC induces NF-κB-dependent upregulation of IL-6 (interleukin-6) transcription by BMSCs which is a growth and anti-apoptotic factor in MM (Chauhan D, et al. *Blood*. 1997; 89:227-234).

MTT/growth inhibition assays revealed that maximal levels of cytotoxicity/growth inhibition were observed at initial CVA21 input doses of 20 TCID₅₀/cell (FIG. 3). Our results reveal that CVA21 has a potent cytotoxic and cytocidal effect against all three multiple myeloma cell lines tested, with reduced cytotoxicity against normal human peripheral blood mononuclear cells (FIG. 3), confirming the cytopathic effect observed following CVA21 infection (FIG. 2).

One ideal attribute of a preferred oncolytic virus is its ability to produce progeny virus which can disseminate to surrounding uninfected tumor cells at local or distant sites to cause further oncolysis. Results indicate that CVA21 was able to replicate efficiently in each of the multiple myeloma cell lines, supporting its use as a replication competent oncolytic agent. CVA21 replication within the different myeloma cell lines resulted in an amplification of the initial input dose of between 100 to 1000-fold in magnitude with no productive virus yield in normal PBMCs infected with CVA21 under the same conditions (FIG. 4).

Another important attribute of a preferred viral oncolytic agent is an optimal level of replication efficiency. From the one-step virus growth curve analysis, CVA21 replicates within MM cells efficiently and rapidly, reaching peak levels of virus production between 8 and 12 h post infection (FIG. 5). This relatively rapid replication cycle may facilitate the capacity of progeny virus to disseminate and control MM disease progression. The replicative capacity and cytotoxicity of CVA21 to inhibit MM cell growth is further evidence to support CVA21 virotherapy of MM, such as treatment of MM in vivo, and selective purging of MM cells ex vivo.

The results reported herein demonstrate that the production of progeny virus, whilst being preferred in order to permit dissemination to surrounding uninfected tumor cells at local or distant sites to cause further oncolysis, is not required for hematologic cancer cell death through oncolytic infection with Picornavirus. The monocytic leukemia cell line U937 was demonstrated herein to be susceptable to CVA (FIG. 12) yet did not demonstrate an observable ability to support CVA21 growth (FIG. 13). Treatment of such cancers may particularly benefit from multiple administration of the Picornavirus.

The exact mechanism by which CVA21 causes the death of MM cells is yet to be determined; the process though would be highly dependent on the cellular transformation events and genetic mutations that exist in the different clinical samples and MM cell lines. CVA21 along with other picornaviruses are thought to mediate cell death through a combination of the shutoff of host cellular protein synthesis, inhibition of transport of cellular glycoproteins, induction of apoptosis and the proteolytic digestion of transcription factors (Rueckert R R. Picornaviridae: The Viruses and Their Replication. In: Fields B N, Knipe D M, Howley P M, eds. *Fields Virology*. Vol. 1. Philadelphia: Lippincott-Raven; 1996:609-645). According to DNA fragmentation assays performed on CVA21 infected RPMI-8226 and NCI-H929 cells, CVA21 is able to induce apoptosis in these two cell lines but not in U266 cells (FIG. 6). U266 cells are dependant on autocrine or paracrine IL-6 stimulation for cell survival and growth. Linked to the activation of cytokine mediated transcription factors like signal transducer and activators of transcription (STAT)-3, the IL-6 signaling pathway may have some influence on the anti-apoptotic response of U266 cells following CVA21 infection.

A recent study (Bharti A C, et al. *Blood*. 2004; 103:3175-3184), confirmed that U266 cells displayed constitutively activated STAT3 in the nuclei of cells, while RPMI-8226 cells were negative for constitutively activated STAT3. Chemical inhibitors of NF-κB however have been shown to induce apoptosis of both U266 and RPMI-8226 cell lines regardless of STAT3 activation, suggesting that STAT3 does not appear to play a role in apoptosis triggered by chemical NF-κB inhibitors. Our results however indicate that the activation of the STAT3 signaling pathway may in fact play an anti-apoptotic role in the oncolysis of CVA21 infected myeloma cells.

The role of the NF-κB family of transcription factors is indeed complex and there is evidence to suggest that NF-κB may play a role in both pro-apoptotic and anti-apoptotic signaling. Novel agents for the treatment of MM, such as thalidomide (Keifer J A, et al. *J Biol. Chem*. 2001; 276:22382-22387), proteasome inhibitor PS-341 (Hideshima T, et al. *Cancer Res*. 2001; 61:3071-3076), and arsenic trioxide $AS_2O_3$ (Kapahi P, et al. *J. Biol. Chem*. 2000; 275:36062-36066), have been shown to inhibit NF-κB activation and help to overcome conventional drug resistance of MM in preclinical and early clinical trials.

Figure 10E:
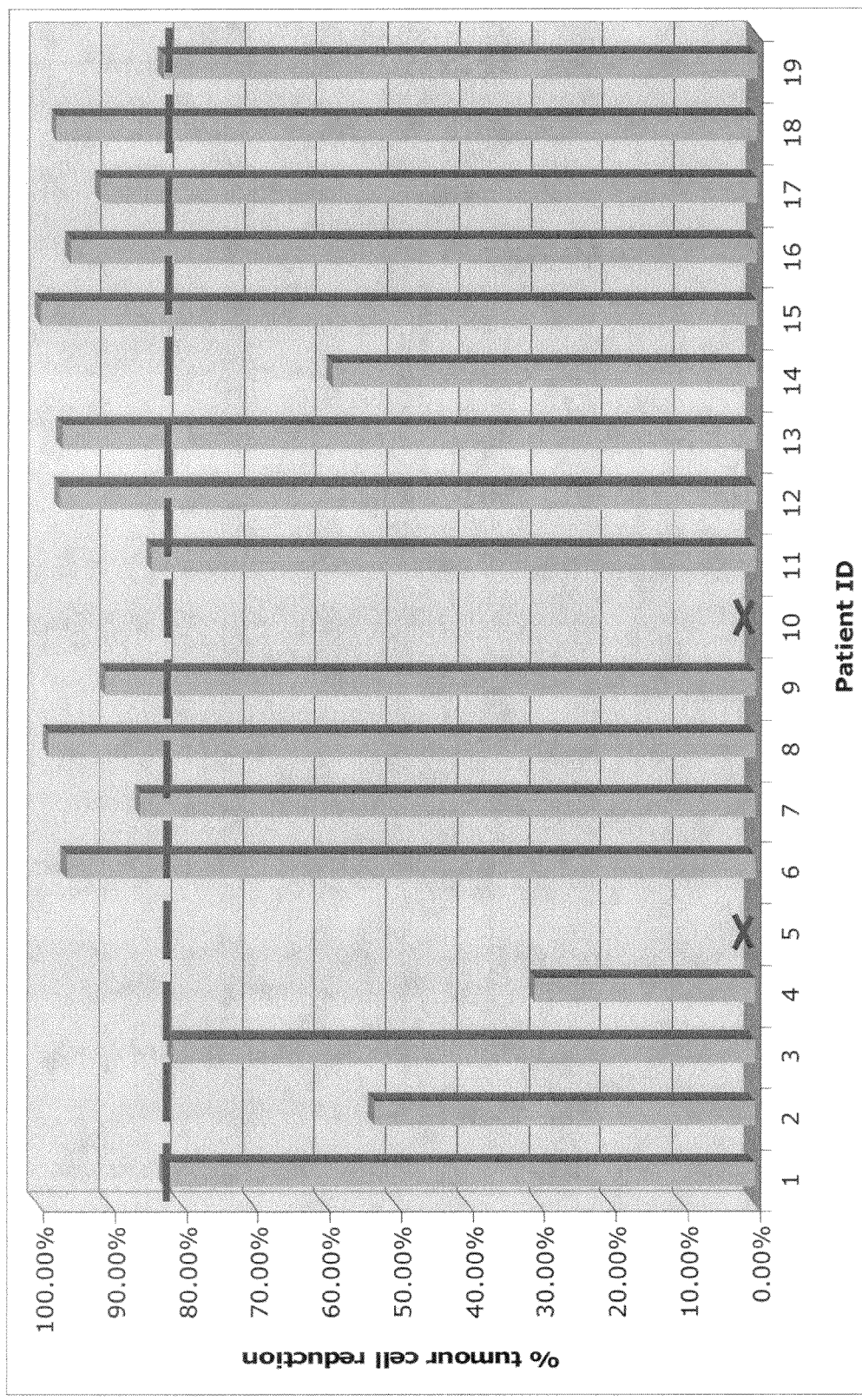
Figure 11A:
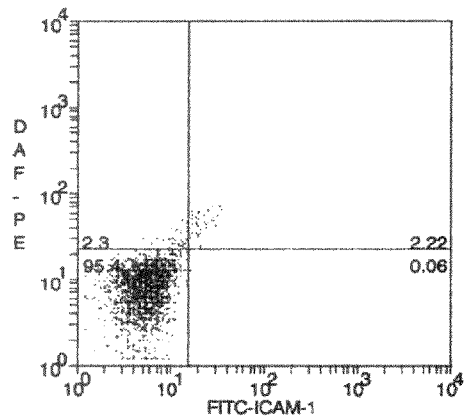
Figure 11A:
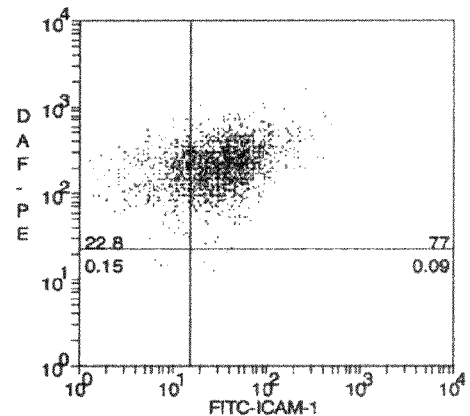
Figure 11A:
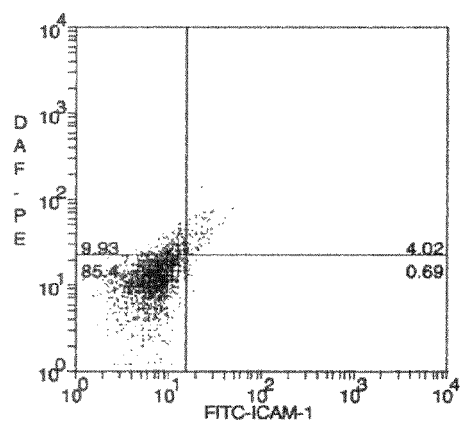
Figure 11A:
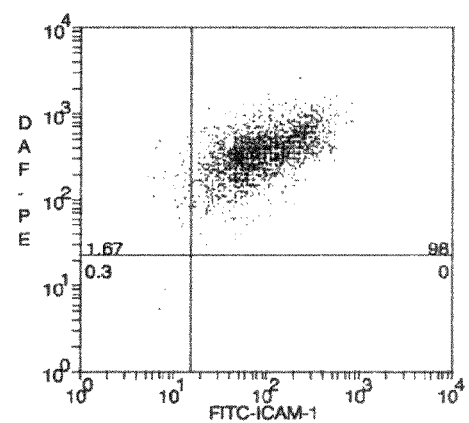
Figure 11A:
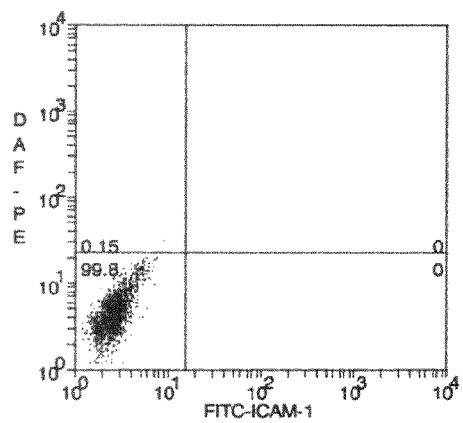
Figure 11A:
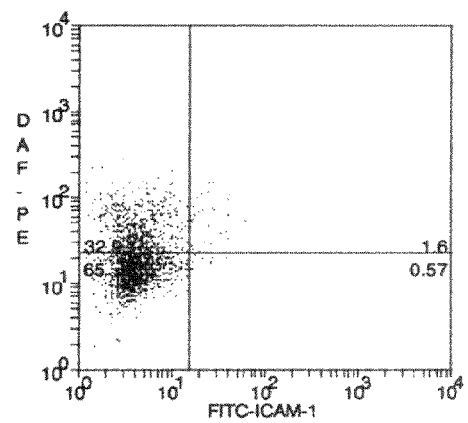
Figure 11B:
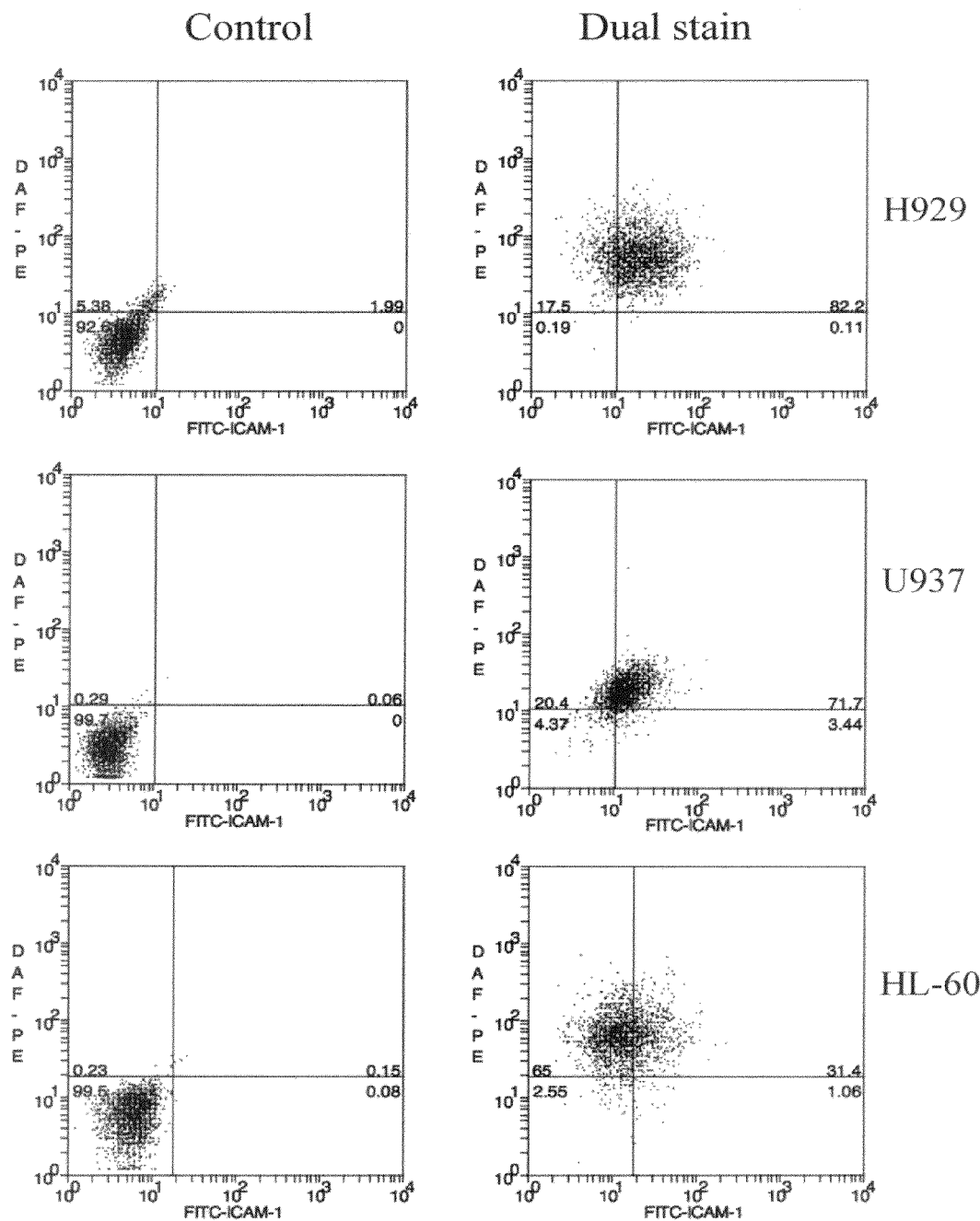

Data collected from clinical samples in this study suggest that the observed oncolytic capacity of CVA21 and other Picornaviruses is not confined to multiple myeloma cell lines, but is also effective in other hematologic cancer cell lines and in primary tumor samples infected ex vivo. The clinical samples had significant levels of CD138 plasma cells present in the bone marrow, all of which expressed ICAM-1 (FIG. 8A) when examined by flow cytometry. Upon infection with increased doses of CVA21, substantial growth arrest and tumor cell purging was observed in all clinical samples, with a maximum of 98% inhibition in one sample (#008). To assess the effect of CVA21 on normal and malignant cells in more detail, cells were stained with anti-CD138 and PI, before analysis using flow cytometry. CVA21 effectively reduced the percentage of malignant cells by >80% in fourteen of the 17 measurable clinical samples (FIG. 10E). Analysis of additional clinical samples (to 19 in total) confirmed the generality of these observations (FIG. 10). An increase in virus input, and extension of CVA21 infection may escalate levels of cancer cell purging. The clinical samples used in this study confirm the beneficial purging of MM cells by CVA21.

The substantial clearance of myeloma tumor cells from patient samples, along with the enduring viability of progenitor stem cells clearly demonstrates that CVA21 is able to specifically kill myeloma cells with relatively minimal impact on normal progenitor cells. In addition, CVA21 treatment was effective on both previously untreated as well as heavily pretreated, chemo-resistant tumor cells, indicating that CVA21 may be a useful therapeutic option for MM. Significant also was the effectiveness of CVA21 at clearing pre-cancerous plasma cells from patients diagnosed with the asymptomatic precursor to EM, MGUS. Up to 30% of such patients go on to develop MM, however it is presently impossible to predict individual prognosis and thus this benign dyscrasia is generally left untreated. The potential use of CVA21 as a prophylaxis in this cohort of patients suggests a novel role for viral therapy as preventative treatment for MM.

CVA21 may also have other roles in the therapy of MM apart from the direct cytotoxic effect on malignant cells. Although most MM cells are initially sensitive to existing drug therapies, drug resistance is a common feature of MM in most cases. The use of CVA21 as a chemosensitizing agent, in combination with agents such as vincristine and doxorubicin may lead to an improved outcome than use of either agent alone and is further reason to investigate CVA21 as a MM therapy.

Currently, there are limited avenues of therapy for multiple myeloma, and new treatments are required. While the immune compromised status of multiple myeloma patients poses a genuine concern for virus therapy of patients with this malignancy, it may be in these patients that CVA21 virotherapy will have the most successful outcome due to the lack of anti-viral immunity. Additionally, MM is a disease characterized by accumulation of slowly proliferating malignant plasma cells, and so provides an ideal opportunity for the effective control of tumor burden by CVA21 oncolysis. Virotherapy has been predicted to be most efficient in slow growing malignancies, as rapidly growing tumors may escape viral oncolysis if the dissemination of progeny virus is not efficient.

Should CVA21 have an adverse outcome in patients, CVA21 infection can be controlled by anti-viral compounds such as pleconaril (Rogers J M, et al. *Adv Exp Med Biol.* 1999; 458:69-76), or immune serum globulin (Rotbart H A. *Pediatr Infect Dis J.* 1999; 18:632-633). Another alternative includes the use of CVA21 for the purging of MM and other hematologic tumor cells ex vivo. Recently the use of oncolytic reovirus as a novel purging strategy for autologous stem cell transplantation was assessed for a range of hematological malignancies, however the purging of enriched ex vivo multiple myeloma cells from admixtures of aphaeresis product was incomplete (Thirukkumaran C M, et al. *Blood.* 2003; 102:377-387). CVA21 is a unique oncolytic virus with selective cytotoxicity against multiple myeloma, cells, and may also have enhanced potential as an ex vivo purging agent.

SUMMARY

Our data demonstrates that CVA21 and other Picornaviruses such as CVA13, CVA15 and CVA18 are effective oncolytic agents against multiple myeloma cell lines and other hematologic cancer cell lines in vitro, with potential applications in the direct oncolysis of MM and hematologic cancer cells in vivo, and in the purging of autologous grafts of peripheral stem cells ex vivo.

While the invention has been described in the manner and detail as above, it will be appreciated by persons skilled in the art that numerous variations and/or modifications including various omissions, substitutions, and/or changes in form or detail may be made to the invention as shown in the specific embodiments without departing from the spirit or scope of the invention as broadly described. The present embodiments are, therefore, to be considered in all respects as illustrative and not restrictive.

REFERENCES

Alain T, et al. Reovirus therapy of lymphoid malignancies. *Blood.* 2002; 100:4146-4153.
Alley M C, et al. Feasibility of drug screening with panels of human tumor cell lines using a microculture tetrazolium assay. *Cancer Res.* 1988; 48:589-601.
Berendt A R, et al. The binding site on ICAM-1 for plasmodium falciparum-infected erythrocytes overlaps, but is distinct from the LFA-1-binding site. *Cell.* 1992; 68:71-81.
Bharti A C, et al. Nuclear factor-{kappa}B and STAT3 are constitutively active in CD138+ cells derived from multiple myeloma patients, and suppression of these transcription factors leads to apoptosis. *Blood.* 2004; 103:3175-3184.
Chauhan D, et al. Multiple myeloma cell adhesion-induced interleukin-6 expression in bone marrow stromal cells involves activation of NF-kappa B. *Blood.* 1996; 87:1104-1112.
Chauhan D, et al. Interleukin-6 inhibits Fas-induced apoptosis and stress-activated protein kinase activation in multiple myeloma cells. *Blood.* 1997; 89:227-234.
Grote D, et al. Live attenuated measles virus induces regression of human lymphoma xenografts in immunodeficient mice. *Blood.* 2001; 97:3746-3754.
Hideshima T, et al. The proteasome inhibitor PS-341 inhibits growth, induces apoptosis, and overcomes drug resistance in human multiple myeloma cells. *Cancer Res.* 2001; 61:3071-3076.
Hideshima T, et al. The role of tumor necrosis factor alpha in the pathophysiology of human multiple myeloma: therapeutic applications. *Oncogene.* 2001; 20:4519-4527.
Hideshima T, et al. NF-kappa B as a therapeutic target in multiple myeloma. *J Biol Chem.* 2002; 277:16639-16647.
Huang Y W, et al. Anti-CD54 (ICAM-1) has antitumor activity in SCID mice with human myeloma cells. Cancer Res. 1995; 55:610-616.
Hughes et al, *J. Gen Virol.* 1989, 70:2943.
Kapahi P, et al. Inhibition of NF-kappa B activation by arsenite through reaction with a critical cysteine in the activation loop of Ikappa B kinase. *J. Biol. Chem.* 2000; 275: 36062-36066.
Keifer J A, et al. Inhibition of NF-kappa B activity by thalidomide through suppression of IkappaB kinase activity. *J Biol. Chem.* 2001; 276:22382-22387.
Remington's Pharmaceutical Science, 15th ed., Mack Publishing Company, Easton, Pa.
Rogers J M, et al. Pleconaril. A broad spectrum antipicornaviral agent. *Adv Exp Med Biol.* 1999; 458:69-76.
Rotbart H A. Antiviral therapy for enteroviral infections. *Pediatr Infect Dis J.* 1999; 18:632-633.
Rueckert R R. Picornaviridae: The Viruses and Their Replication. In: Fields B N, Knipe D M, Howley P M, eds. *Fields Virology.* Vol. 1. Philadelphia: Lippincott-Raven; 1996: 609-645.
Schirrmacher V, et al. Antitumor effects of Newcastle Disease Virus in vivo: local versus systemic effects. *Int J Oncol.* 2001; 18:945-952),
Schmidt, N. J., et al, *Proc. Soc. Exp. Biol. Med.,* 1961, 107:63.
Schwab G, et al. Characterization of an interleukin-6-mediated autocrine growth loop in the human multiple myeloma cell line, U266. *Blood.* 1991; 77:587-593.
Shafren D. et al *J. Virol* 1997, 71:4736.
Shafren D R, et al. Systemic therapy of malignant human melanoma tumors by a common cold-producing enterovirus, coxsackievirus a21. *Clin Cancer Res.* 2004; 10:53-60).
Sickles G. M., *Proc. Soc. Exp. Biol. Med.* 102:742.
The Merck Index, Thirteenth Edition, Merck & Co. Inc, Whitehouse Station, N.J. USA.,
Thirukkumaran C M, et al. Reovirus oncolysis as a novel purging strategy for autologous stem cell transplantation. *Blood.* 2003; 102:377-387.
PCT/AU00/01461 (WO 01/37866) entitled "A Method of Treating a Malignancy in a Subject and a Pharmaceutical Composition For Use in Same")
PCT/AU2003/001688 (WO2004/054613) entitled "A method of treating a malignancy in a subject via direct Picornaviral-mediated oncolysis").
PCT/AU2005/000048 entitled "Modified oncolytic viruses".

The invention claimed is:
1. A method for treating and/or preventing hematologic cancer in a subject, the method comprising administering a therapeutically effective amount of a Picornavirus or a modified form thereof such that at least some cells of the cancer undergo viral oncolysis, wherein said administration comprises ex vivo purging by said Picornavirus, or modified form thereof, of malignant cells within auto grafts prior to autologous stem cell transplantation, or comprises ex vivo purging of malignant cells within auto grafts prior to transplantation, wherein the auto grafts comprise hematopoietic stem cells.

2. The method according to claim 1, wherein the Picornavirus is selected from the group consisting of prototype and clinically isolated strains of enteroviruses.

3. The method according to claim 1, wherein the enterovirus is selected from the group consisting of Coxsackievirus, Echovirus, Poliovirus, unclassified enteroviruses, Rhinovirus, Paraechovirus, Hepatovirus, and Cardiovirus.

4. The method according to claim 1, wherein the Picornavirus is a Coxsackie A group virus selected from the group consisting of CVA13, CVA15, CVA18, CVA20, CVA21, modified forms thereof, and combinations thereof.

5. The method according to claim 1, wherein the range of viral dose is between about 0.01 to about 1000 plaque forming units (PFU).

6. The method according to claim 1, wherein the hematologic cancer is a cancer selected from the group consisting of multiple myeloma, B cell lymphoma, B prolymphocytic leukemia and monocytic leukemia.

7. The method according to claim 1, wherein cells of the hematologic cancer over-express the virus-cell entry receptor molecules intercellular adhesion molecule-1 (ICAM-1) and/or decay-accelerating factor (DAF).

8. The method according to claim 1, wherein cells of the hematologic cancer constitutively express NF-$_\kappa$B.

9. The method according to claim 1, wherein the subject is a human.

* * * * *